United States Patent
Yeo et al.

(10) Patent No.: US 10,398,651 B2
(45) Date of Patent: Sep. 3, 2019

(54) CARRIER-FREE NANOPARTICLES

(71) Applicant: Purdue Research Foundation, West Lafayette, IN (US)

(72) Inventors: Yoon Yeo, West Lafayette, IN (US); Joonyoung Park, West Lafayette, IN (US); Bo Sun, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

(21) Appl. No.: 15/624,303

(22) Filed: Jun. 15, 2017

(65) Prior Publication Data

US 2017/0360709 A1 Dec. 21, 2017

Related U.S. Application Data

(60) Provisional application No. 62/351,185, filed on Jun. 16, 2016.

(51) Int. Cl.
| | |
|---|---|
| *A61K 9/16* | (2006.01) |
| *A61K 31/337* | (2006.01) |
| *A61K 9/00* | (2006.01) |
| *A61K 47/10* | (2017.01) |
| *A61K 9/51* | (2006.01) |

(52) U.S. Cl.
CPC ............ *A61K 9/167* (2013.01); *A61K 9/0019* (2013.01); *A61K 9/1641* (2013.01); *A61K 9/1652* (2013.01); *A61K 9/1658* (2013.01); *A61K 9/5161* (2013.01); *A61K 9/5169* (2013.01); *A61K 9/5192* (2013.01); *A61K 31/337* (2013.01); *A61K 47/10* (2013.01)

(58) Field of Classification Search
CPC .... A61K 9/167; A61K 9/1658; A61K 9/1652; A61K 9/1641; A61K 31/337; A61K 9/0019; A61K 47/10
See application file for complete search history.

(56) References Cited

PUBLICATIONS

Ying Lu, et al, Development and Evaluation of Transferrin-Stabilized Paclitaxel Nanocrystal Formulation, 176 J Control. Rel. 76 (Year: 2014).*
Merisko-Liversidge, E.M. and G.G. Liversidge, Drug Nanoparticles: Formulating Poorly Water-Soluble Compounds. Toxicol Pathol, 2008. 36(1): p. 43-48.
Yuan, F., et al., Vascular permeability in a human tumor xenograft: molecular size dependence and cutoff size. Cancer Res, 1995. 55(17): p. 3752-6.
Lu, Y., et al., Development and evaluation of transferrin-stabilized paclitaxel nanocrystal formulation. J Control Release, 2014. 176: p. 76-85.
Murakami, M., et al., Docetaxel Conjugate Nanoparticles That Target alpha-Smooth Muscle Actin-Expressing Stromal Cells Suppress Breast Cancer Metastasis. Cancer Res, 2013. 73(15): p. 4862-71.

* cited by examiner

*Primary Examiner* — Sean M Basquill
(74) *Attorney, Agent, or Firm* — Purdue Research Foundation; Yonghao Hou

(57) ABSTRACT

A carrier free nanoparticle formulation with good circulation stability is made for anticancer drug delivery. Nanocrystals crystallized in the medium containing Pluronic F-127 then coated with albumin (Cim-F-Alb) had the smallest size and the most native albumin, and showed most favorable cell interaction profiles and better stability than commercial albumin based Abraxane formulation, while maintaining comparable cytotoxicity to those of Abraxane and solvent-dissolved paclitaxel (PTX).

12 Claims, 36 Drawing Sheets

FIG. 4A
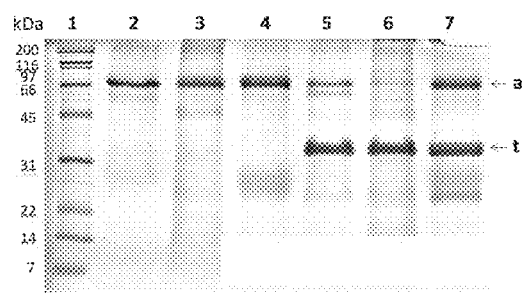
FIG. 4B
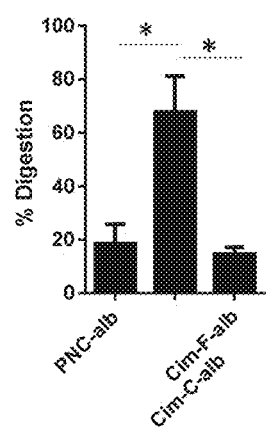
FIG. 4C
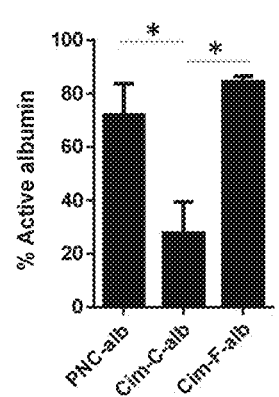
FIGURE 4

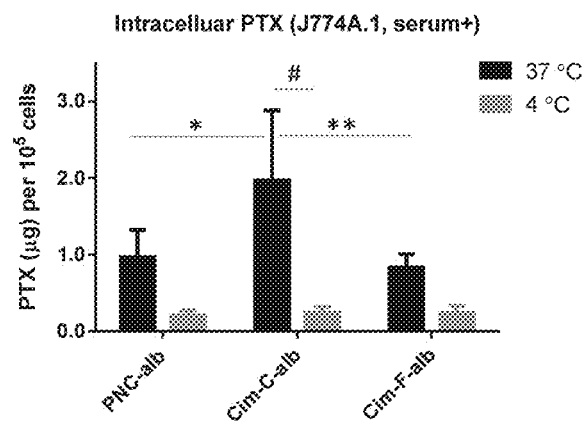
FIG. 5A
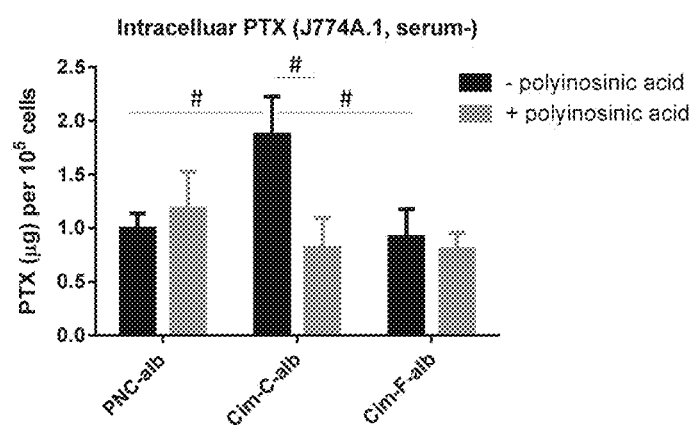
FIG. 5B
FIGURE 5

FIG. 7A
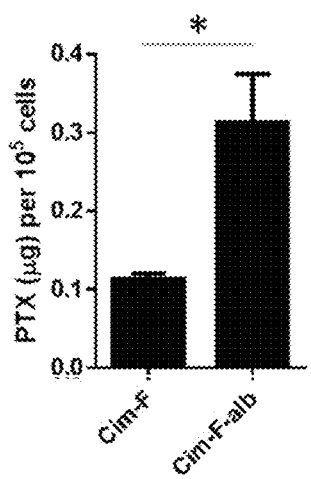
FIG. 7B
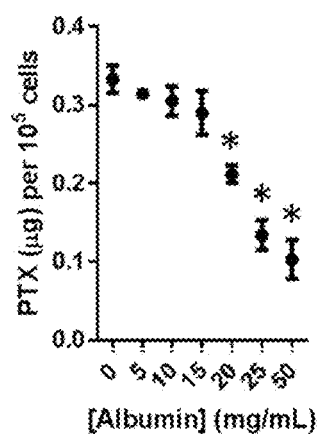
FIG. 7C
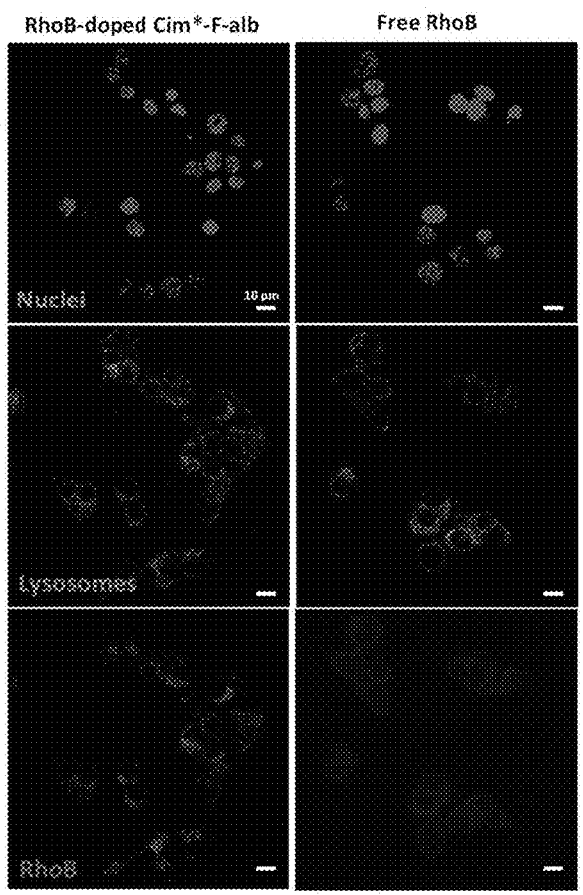
FIG. 7D
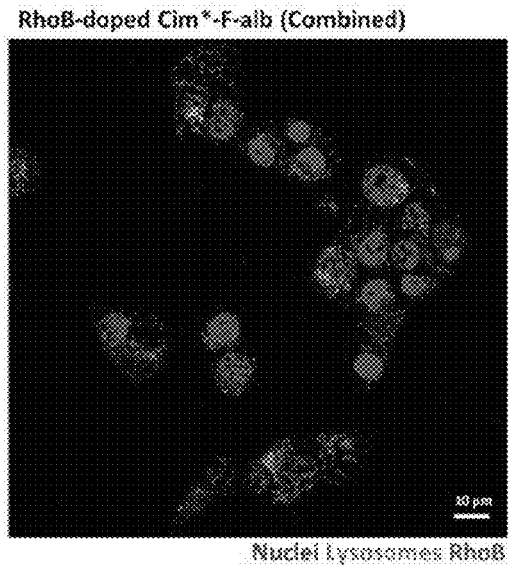
FIGURE 7

FIG. 8A
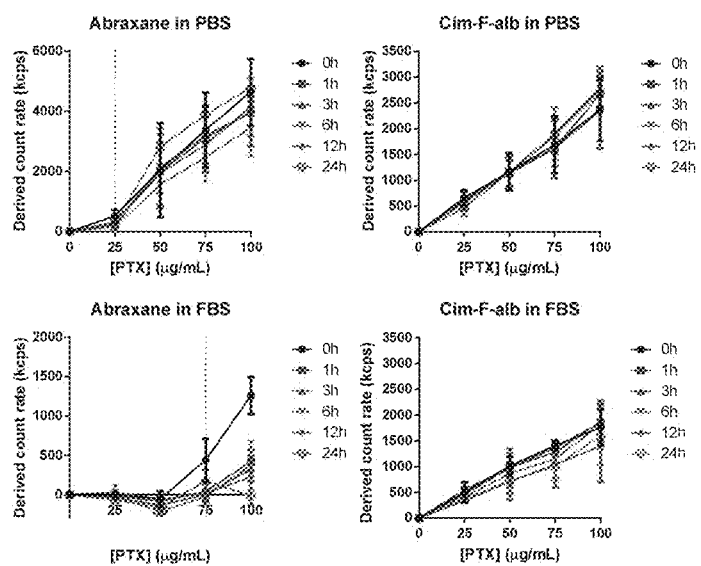
FIG. 8B
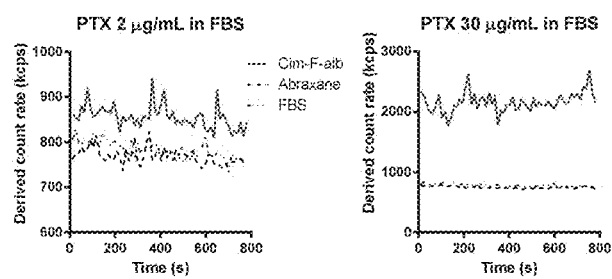
FIGURE 8

FIG. 10A
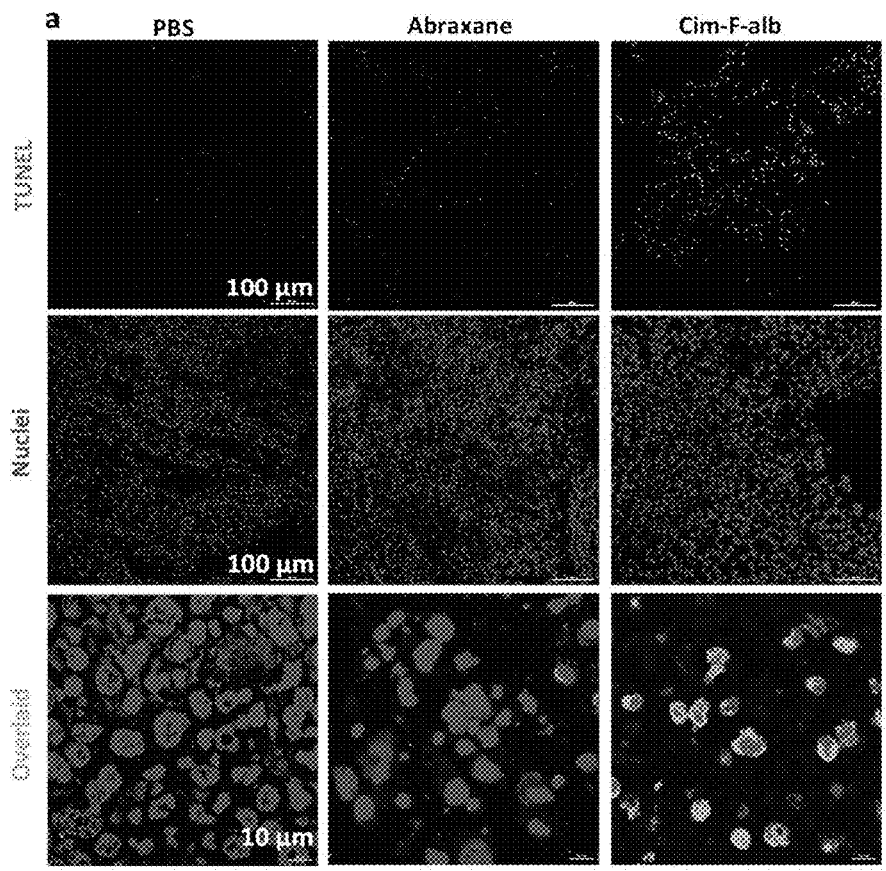
FIG. 10B
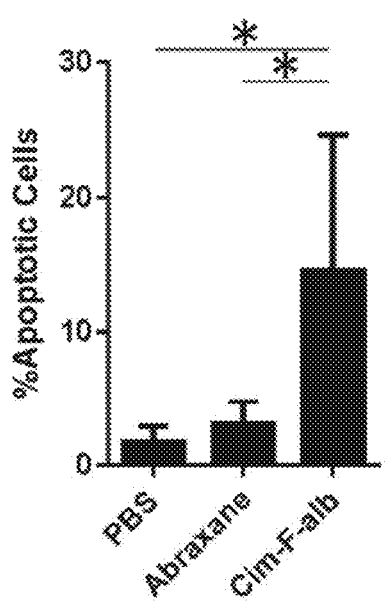
FIG. 10C
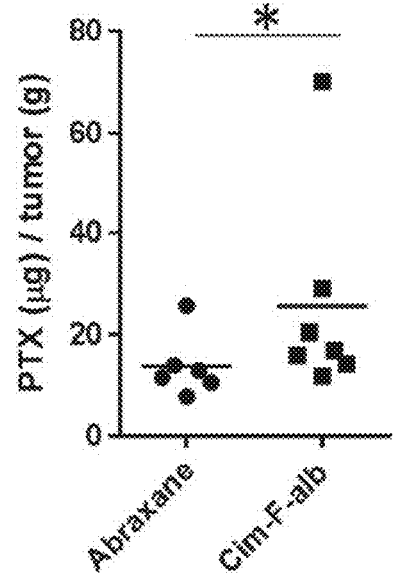
FIGURE 10

FIG. 11A
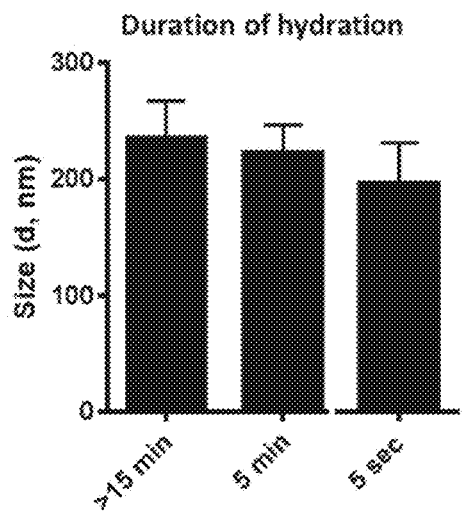
FIG. 11B
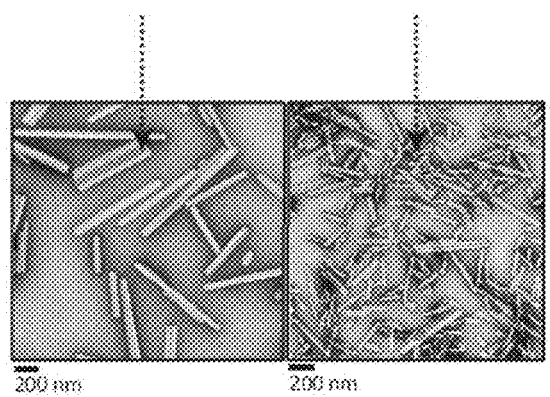
FIG. 11C
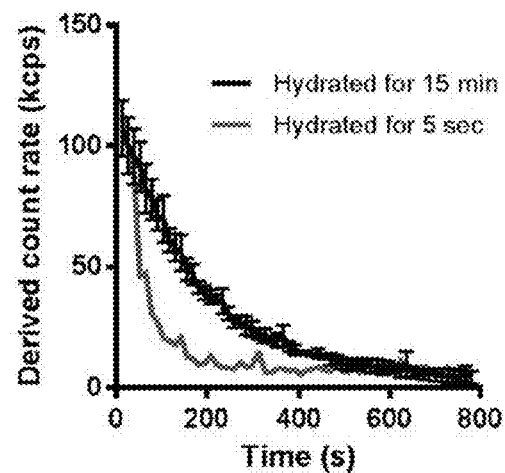
FIGURE 11

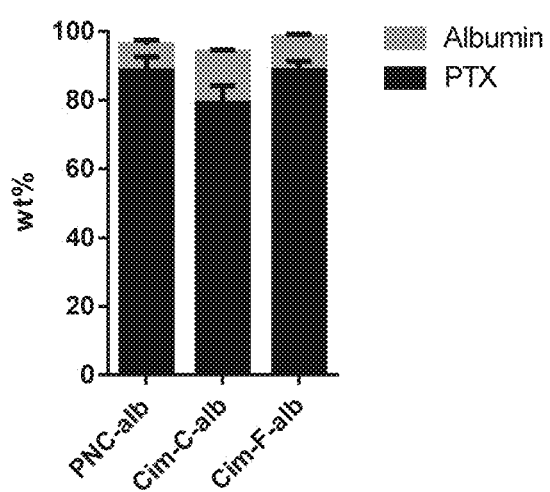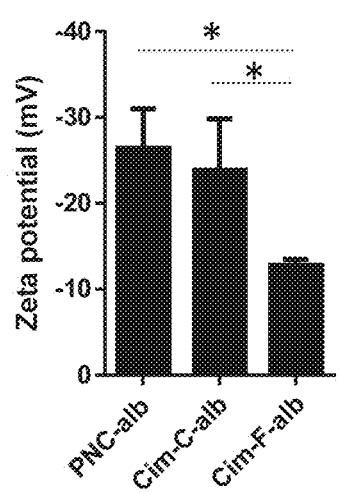
FIG. 13A  FIG. 13B
FIGURE 13

FIG. 23A
PTX dissolved in 6h
FIG. 23B
Dissolved PTX in FBS (6h)
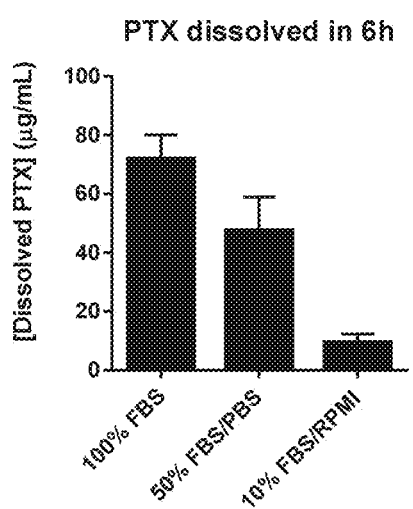
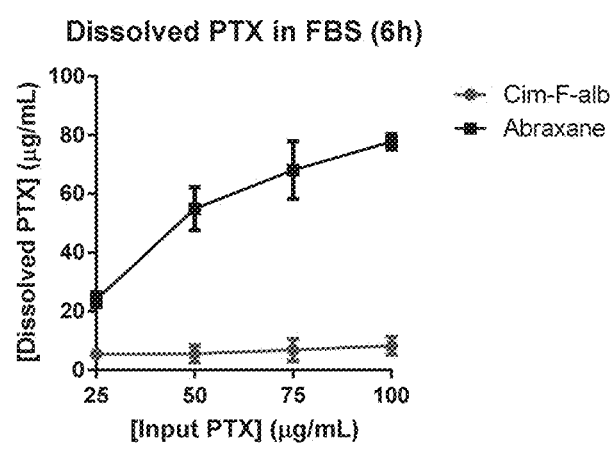
FIGURE 23

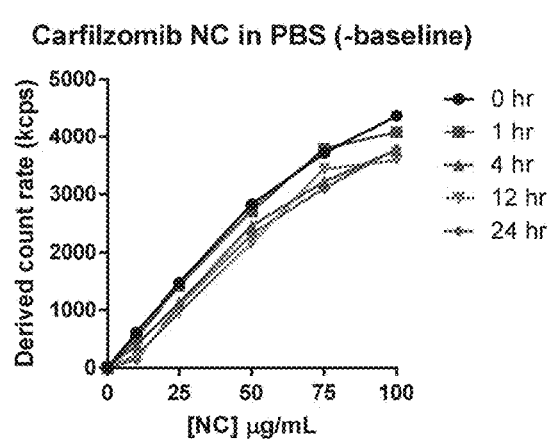
FIG. 33A
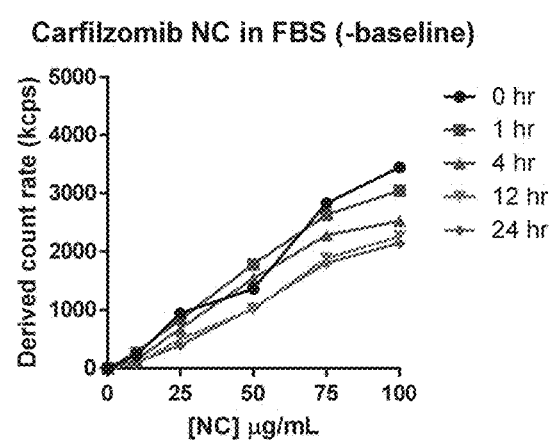
FIG. 33B
FIGURE 33

Docetaxel/Cim-F-alb

TEM image

SEM image

FIG. 35A
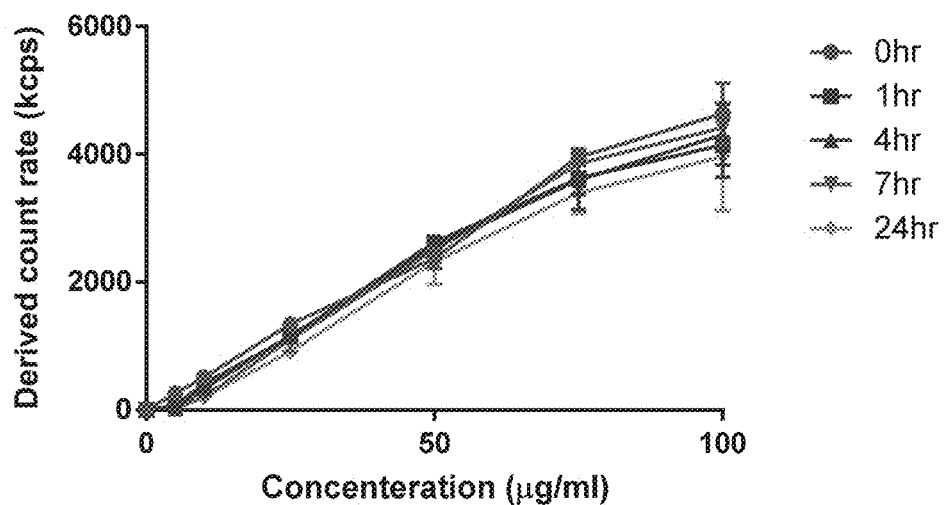
FIG. 35B
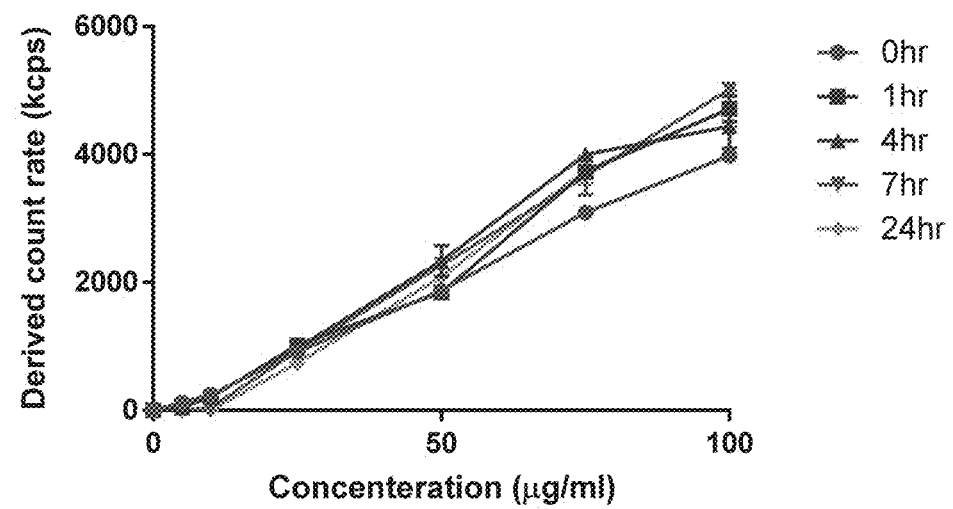
FIGURE 35

CARRIER-FREE NANOPARTICLES

This application claims the benefit of U.S. Provisional application No. 62/351,185 under 35 U.S.C. 119 (e), filed on Jun. 16, 2016. The content of which is expressly incorporated herein entirely.

This invention was made with government support under R01EB017791 awarded by the National Institutes of Health. The government has certain rights in the invention.

TECHNICAL FIELD

The present disclosure generally relates to carrier-free nanoparticles, and in particular to nanocrystals stabilized with a native form of albumin layer.

BACKGROUND

This section introduces aspects that may help facilitate a better understanding of the disclosure. Accordingly, these statements are to be read in this light and are not to be understood as admissions about what is or is not prior art.

Current anti-cancer drugs and other drugs have exhibited poor water solubility and thus poor drug distribution to target sites such as tumors. There is therefore an unmet need for methods and compositions that permit maximization of benefits of drugs.

SUMMARY

This disclosure provides a carrier-free nanoparticle comprising a drug crystalline, formed in a surfactant-containing medium, coated with a native protein or polysaccharide, wherein the protein/polysaccharide to the drug crystalline ratio ranges from about 1:10 to about 5:10 and the nanoparticle ranges in size between about 100 nm to about 300 nm.

In some embodiment the aforementioned drug crystalline is paclitaxel (PTX).

In some embodiment the aforementioned surfactant is Pluronic F-127.

In some embodiment the aforementioned native protein is albumin (Alb).

In some embodiment the aforementioned polysaccharide comprises at least one of hyaluronic acid, chondroitin sulfate, heparin, chitosan, or their derivatives.

In some embodiment the aforementioned native protein is selected from the group consisting of albumin, transferrin, antibodies and the combination thereof.

In some embodiment the aforementioned surfactant is Pluronic F127 or Cetyltrimethylammonium Bromide (CTAB).

In some embodiment the aforementioned drug is water-insoluble.

In some embodiment the aforementioned drug has prolonged circulation time with improved interaction with target cells.

This disclosure further provides a method for making carrier-free nanoparticles. The method comprises the steps of:

crystallizing a drug in a surfactant-containing medium to form a crystalline incipient film;

hydrating the crystalline incipient film with bath sonication to form hydrated suspension; and stabilizing the hydrated suspension with a surface modifier, wherein said surface modifier is adsorbed on the crystalline surface by the surfactant.

In some embodiment the aforementioned method uses albumin as the surface modifier.

In some embodiment the aforementioned method uses polysaccharide as the surface modifier.

In some embodiment the aforementioned method uses polysaccharide selected from hyaluronic acid, chondroitin sulfate, heparin, chitosan, or their derivatives.

In some embodiment the aforementioned method uses the surface modifier to the crystalline ratio ranging from about 1:10 to about 5:10.

In some embodiment the aforementioned method uses Pluronic F-127 as the surfactant.

These and other features, aspects and advantages of the present invention will become better understood with reference to the following figures, associated descriptions and claims.

BRIEF DESCRIPTION OF DRAWINGS

FIG. 3A Particle size of NC with and without albumin coating as a function of the number of centrifugation, measured by DLS. FIG. 3B TEM images and size analysis. TEM images of PNC-alb, Cim-C-alb, and Cim-F-alb were analyzed for size distribution. Scale bars: 500 nm.

FIG. 4. FIG. 4A Representative SDS-PAGE gel image of pulse proteolysis. PNC-alb, Cim-C-alb, and Cim-F-alb were incubated with thermolysin for 5 min. Lanes 1: size markers; Lane 2: PNC-alb; Lane 3: Cim-C-alb, Lane 4: Cim-F-alb; Lane 5: PNC-alb+thermolysin; Lane 6: Cim-C-alb+thermolysin; and Lane 7: Cim-F-alb+thermolysin. 'a' denotes albumin (66 kDa), and 't' denotes thermolysin (35 kDa). FIG. 4B % Digestion of albumin. % digested albumin was determined by albumin band intensity after proteolysis/albumin band intensity prior to proteolysis. n=4 independently and identically performed experiments. FIG. 4C Active albumin content estimated by esterase assay. % active albumin was calculated by dividing esterase active albumin/the amount of albumin determined by SDS-PAGE. n=3 independently and identically performed experiments. *: $p<0.01$ by Tukey's multiple comparisons test.

FIG. 5. FIG. 5A PTX uptake by J774A.1 macrophages after 30 min incubation with PNC-alb, Cim-C-alb, and Cim-F-alb (equivalent to 30 µg/mL PTX) at 4° C. or 37° C. n=3 independently and identically performed experiments. FIG. 5B PTX uptake by J774A.1 macrophages after 30 min incubation with PNC-alb, Cim-C-alb, and Cim-F-alb (equivalent to 30 µg/mL PTX) with and without pre-treatment of polyinosinic acid. n=4 independently and identically performed experiments. *: $p<0.05$; **: $p<0.01$; #: $p<0.001$ by Sidak's multiple comparisons test.

FIG. 6A PTX uptake by B16F10 melanoma cells after 3 h incubation with PNC-alb, Cim-C-alb, and Cim-F-alb (equivalent to 30 µg/mL PTX). FIG. 6B-C Cytotoxicity of NC in B16F10 cells measured after 3 h incubation with NC and 21 h additional incubation in treatment-free medium, measured by propiodium iodide staining and flow cytometry FIG. 6B and MTT assay FIG. 6C. n=3 independently and identically performed experiments (a, b). n=5 measurements FIG. 6C. *: $p<0.05$ by Tukey's multiple comparisons test.

FIG. 7. FIG. 7A PTX uptake by B16F10 cells after 3 h incubation with Cim-F or Cim-F-alb (equivalent to 30 µg/mL PTX). n=3 independently and identically performed experiments; *: $p<0.01$ by unpaired two-tailed t-test. FIG.

7B PTX uptake by B16F10 cells after 3 h incubation with Cim-F-alb (equivalent to 30 µg/mL PTX) in the presence of extra albumin. n=3 independently and identically performed experiments; *: p<0.01 by Tukey's multiple comparison test vs. no albumin control. FIG. 7C Intracellular localization of rhodamine B doped Cim*-F-alb (left) or free Rhodamine B (right) in B16F10 cells after 30 min incubation. FIG. 7D Overlay image of all fluorescence channels of B16F10 cells incubated with rhodamine B doped Cim*-F-alb.

FIG. 8. FIG. 8A Derived count rate of Cim-F-alb and Abraxane in PBS (top) and undiluted FBS (bottom) at 37° C. For samples in FBS, the values were obtained by subtracting the derived count rate of FBS from those of particle suspensions in FBS at each time point. n=3 independently and identically performed experiments; FIG. 8B Dissolution rate of Cim-F-alb, PNC, and Abraxane in FBS at PTX FIG. 9. In vivo activity of Cim-F-alb and Abraxane in C57BL/6 mice.

FIG. 10. FIG. 10A Representative photographs of deoxynucleotidyl transferase-mediated deoxyuridine triphosphate nick end (TUNEL)-stained B16F10 tumor sections. FIG. 10B Quantitative analysis of TUNEL-stained sections. % apoptotic cells=number of apoptotic cells/total number of nuclei measured by ImageJ. Data are represented as averages and standard deviations of 12 images for PBS- and Abraxane groups and 14 images for Cim-F-alb group (2 images from each tumor section). *: p<0.01 by Tukey's multiple comparisons test. FIG. 10C PTX content in B16F10 tumor tissues. n=6 for Abraxane and n=7 for Cim-F-alb group. Horizontal bars=means. *: p<0.05 by Mann-Whitney test.

FIG. 11. FIG. 11A Size of Cim-F-alb as a function of hydration time (n=9 for >15 min hydration and n=3 for 5 min and 5 sec hydration). FIG. 11B TEM images of Cim-F-alb prepared with >15 min hydration (left) or 5 sec hydration (right). FIG. 11C Dissolution rate of Cim-F-alb (eq. to PTX 2 µg/mL) prepared with 15 min hydration (black) or 5 sec (red) in PBS containing 0.2% Tween80.

FIG. 13. FIG. 13A PTX and protein contents in each PTX NC formulation, determined by HPLC and SDS-PAGE, respectively. n=4 independently and identically performed experiments. FIG. 13B Zeta potential of NC, measured in phosphate buffer (pH 7.4, 1 mM). n=3 independently and identically performed experiments. *: p<0.05 by Tukey's multiple comparisons test.

FIG. 16A Cytotoxicity of Pluronic F127 in B16F10 cells after 3 h exposure, measured by MTT assay (n=3 measurements). FIG. 16B Cytotoxicity of PNC-alb, Cim-F-alb, and a mixture of PNC-alb and 10 µg/mL F127 in B16F10 cells after 3 h exposure, measured by MTT assay (n=3 measurements). *: p<0.01 by Tukey's multiple comparisons test.

FIG. 23. FIG. 23A Amorphous as-received PTX dissolved in undiluted FBS, 50% FBS/PBS, and 10% FBS/RPMI after 6 h incubation. One milligram of PTX was added to 1 mL of each medium and incubated for 6 h with agitation. A supernatant was separated from the undissolved PTX by centrifugation at 135,700 rcf for 10 min, extracted with 3 mL of ethyl acetate, which was evaporated and reconstituted in 50% ACN for HPLC analysis. FIG. 23B Abraxane and Cim-F-alb dissolved in undiluted FBS after 6 h incubation. The FBS suspension was sampled at 6 h to quantify dissolved PTX by that time. A supernatant was separated from the sample by 10 min centrifugation at 135,700 rcf and analyzed in the same way. The incubation time was limited to 6 h due to the instability of PTX in serum [1, 2]. Since the extraction method cannot differentiate protein-bound PTX from free PTX, the measured values represent the sum of serum protein-bound and free PTX.

[1] G. Bajaj, M. R. Kim, S. I. Mohammed, Y. Yeo, Hyaluronic acid-based hydrogel for regional delivery of paclitaxel to intraperitoneal tumors, J. Control. Release 158 (2012) 386-392.

[2] I. Ringel, S. B. Horwitz, Taxol is converted to 7-epitaxol, a biologically active isomer, in cell culture medium, J. Pharmacol. Exp. Ther. 242 (1987) 692-698.

Figure 24:
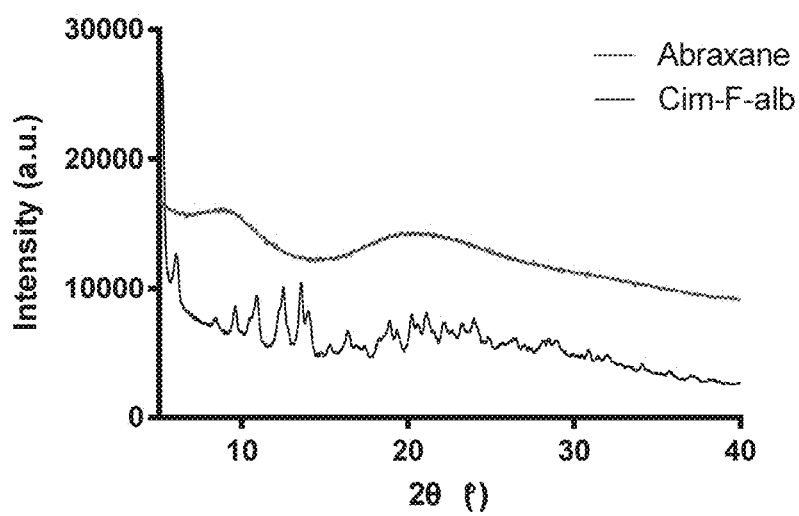

FIG. 24. X-ray powder diffraction patterns of Abraxane and Cim-F-alb.

Figure 25:
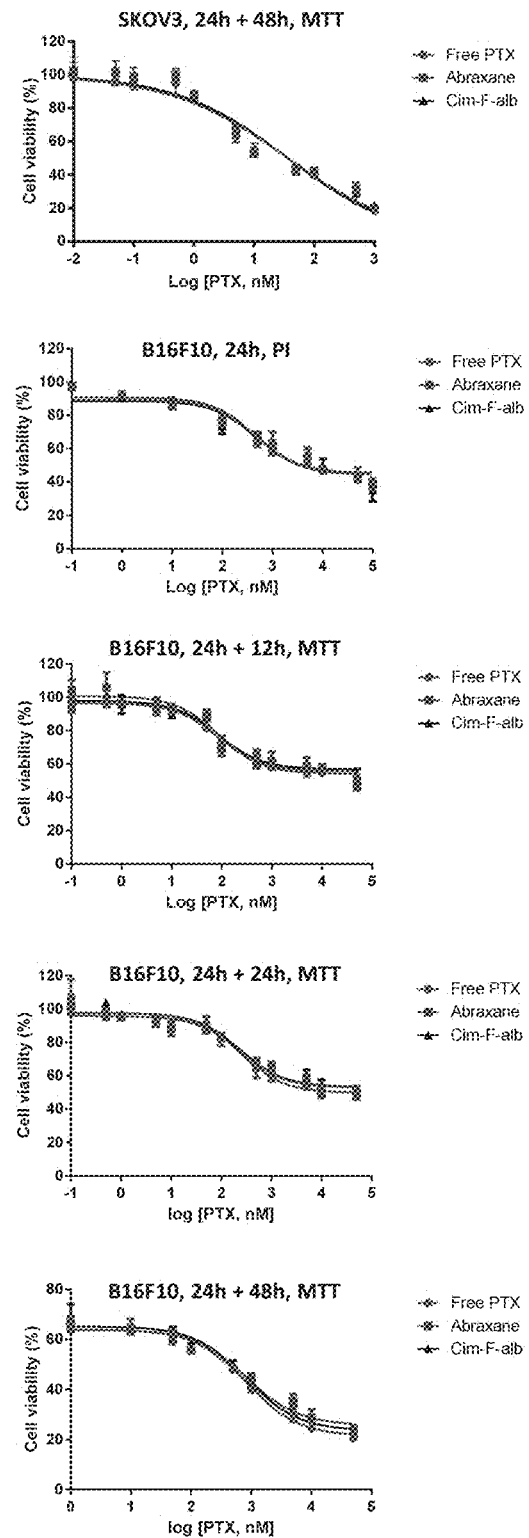

FIG. 25. Cytotoxicity of Cim-F-alb, Abraxane, and free PTX in SKOV-3 human ovarian cancer cells measured by MTT assay (n=4 measurements) and B16F10 melanoma cells measured by PI staining and flow cytometry (n=2 independently and identically performed experiments) and MTT assay (n=3 measurements) varying the post-treatment incubation time.

Figure 26:
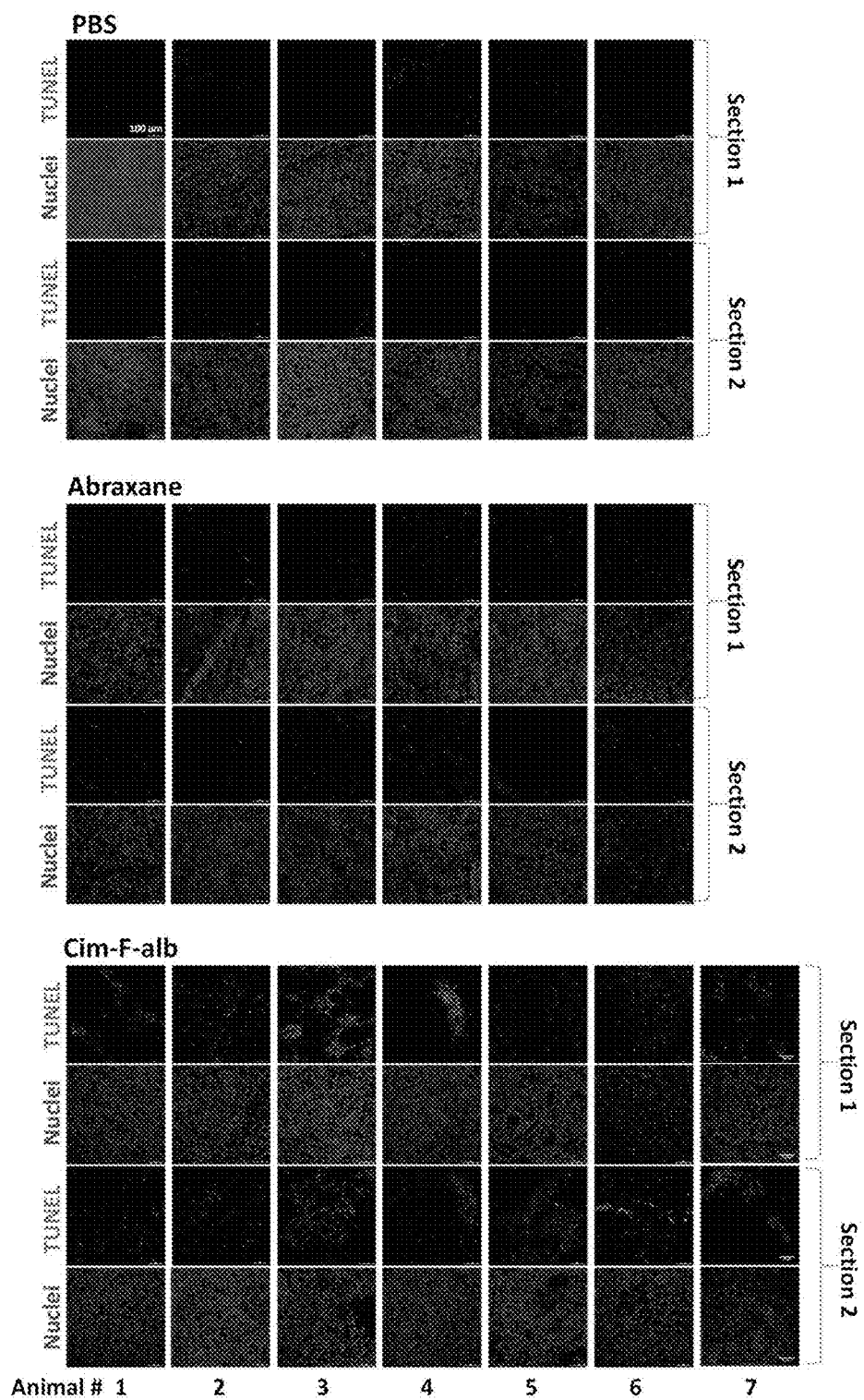

FIG. 26. All images of TUNEL-stained B16F10 tumor sections. Two randomly selected fields were imaged for each animal in the PBS, Abraxane and Cim-F-alb treatment groups (n=6 for PBS, Abraxane; n=7 for Cim-F-alb).

Figure 27:
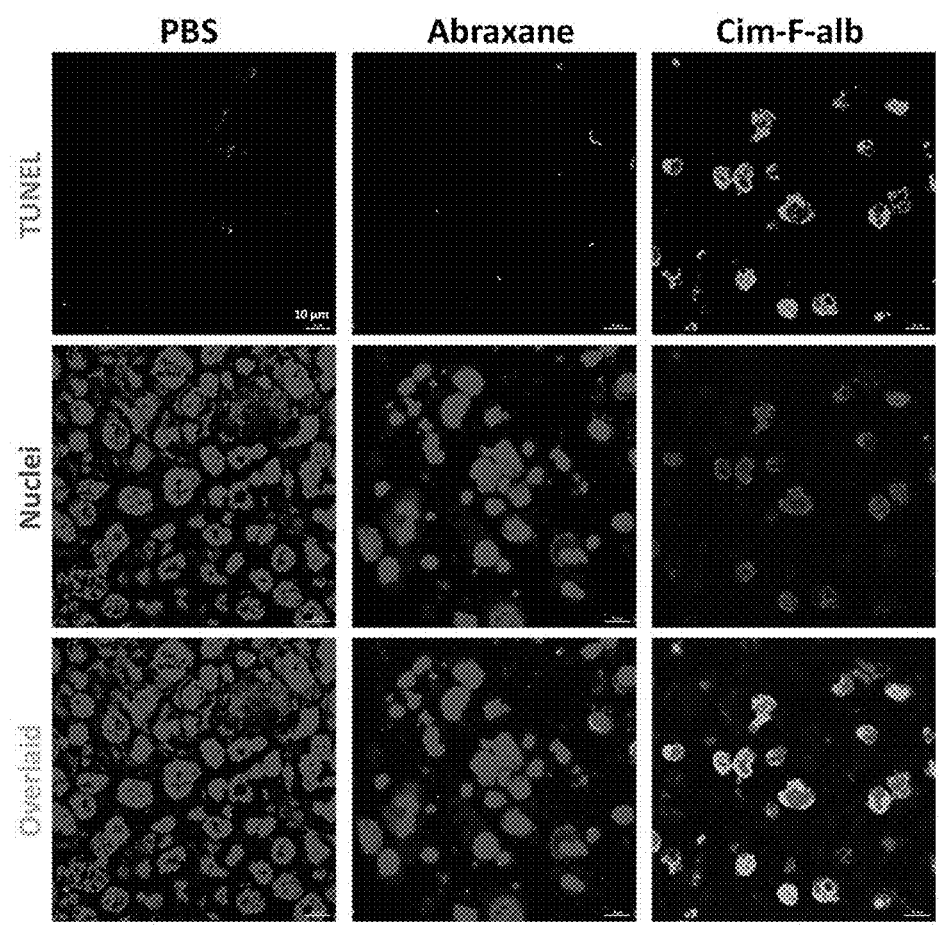

FIG. 27. TUNEL stained B16F10 tumor section at high magnification indicating colocalization of TUNEL signal and nuclei stain.

Figure 28:
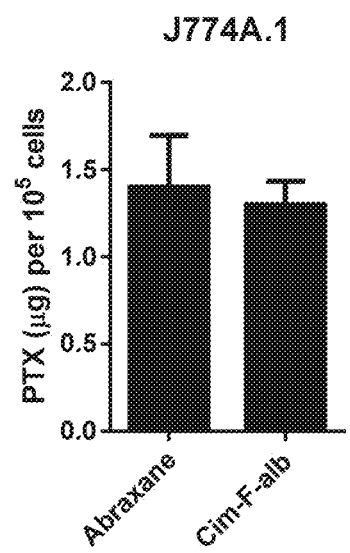
Figure 28:
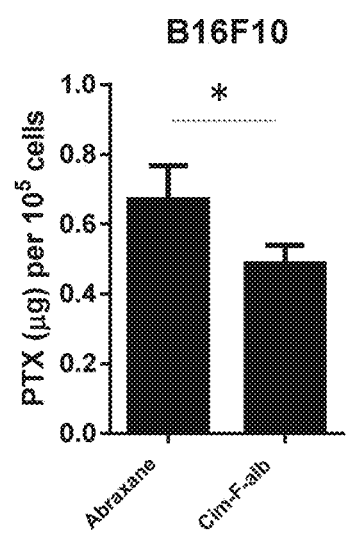

FIG. 28. Uptake of Abraxane and Cim-F-alb by FIG. 28A J774A.1 macrophages and FIG. 28B B16F10 melanoma cells. Cim-F-alb and Abraxane (eq. to 30 µg PTX/mL) were incubated with J774A.1 cells for 30 min or with B16F10 cells for 3 h at 37° C. Intracellular PTX content was determined by HPLC and normalized with the number of analyzed cells. Data are presented as averages and standard deviations of 3 independently and identically performed experiments. *: $p<0.05$ by unpaired t-test.

Figure 29:
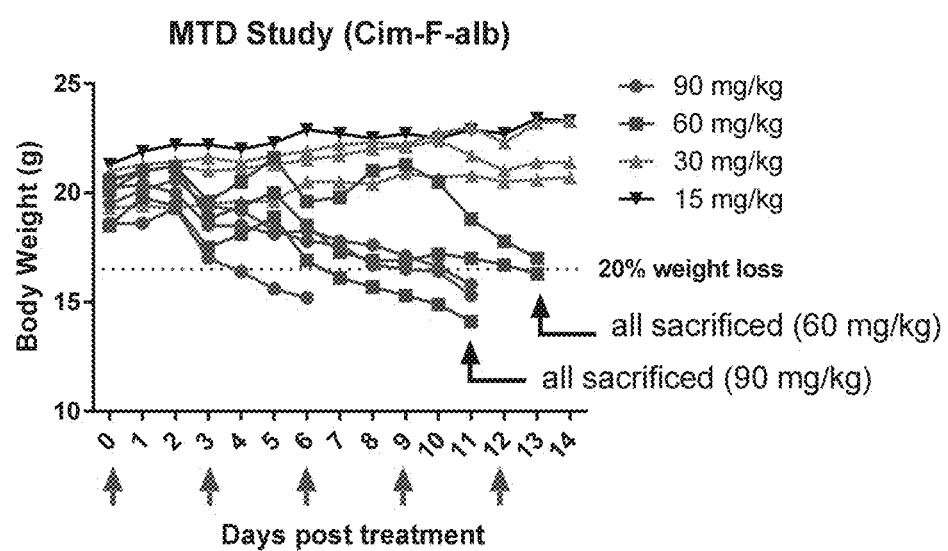

FIG. 29. Body weight change of each animal receiving different doses of Cim-F-alb.

Figure 30:
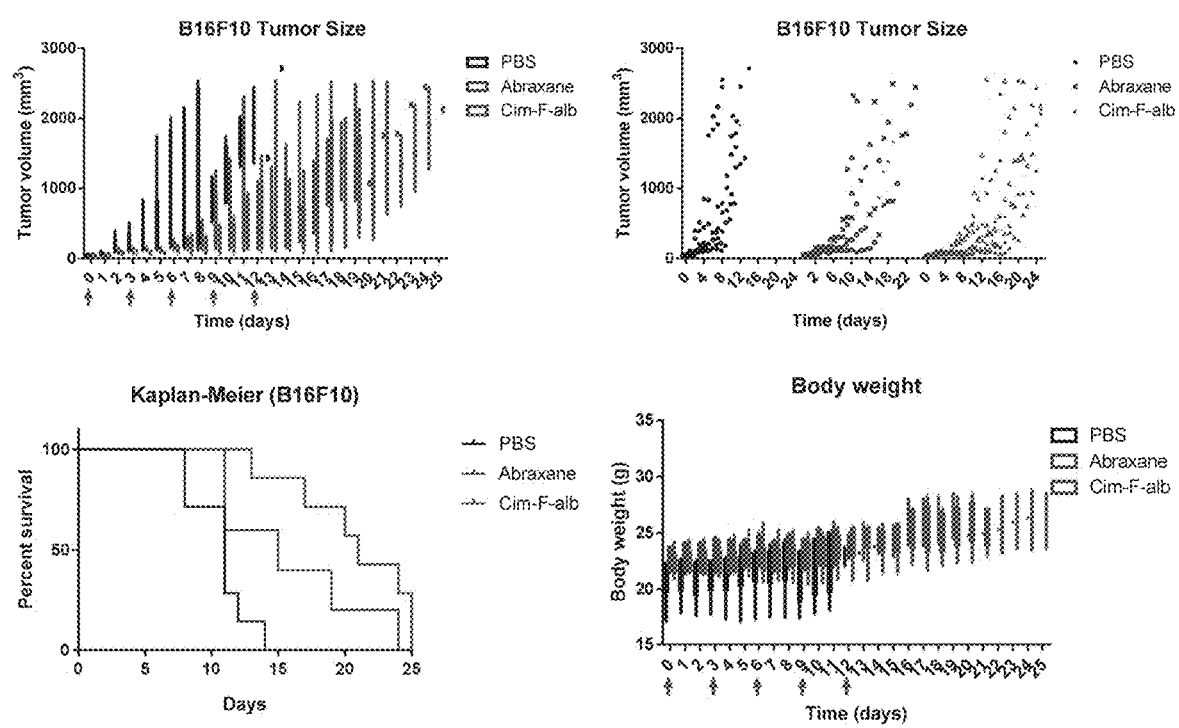

FIG. 30. Tumor size change, survival, and body weight change of animals treated with Abraxane or Cim-F-alb at 30 mg/kg×5 times FIG. 31. PTX concentrations in FIG. 31A blood or FIG. 31B major organs of animals treated with Abraxane or Cim-F-alb (30 mg/kg PTX)

Figure 32:
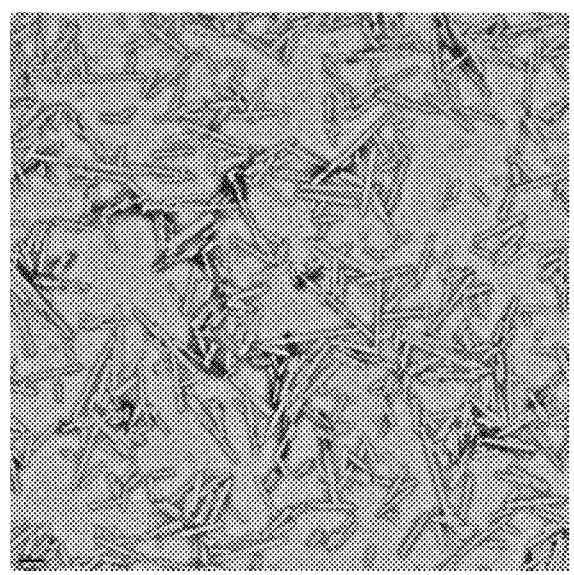

FIG. 32. TEM image of CFZ/Cim-F-alb

FIG. 33. FIG. 33A Derived count rate of CFZ/Cim-F-alb in PBS (left) and FIG. 33B undiluted FBS (right) at 37° C. over 24 h.

Figure 34:
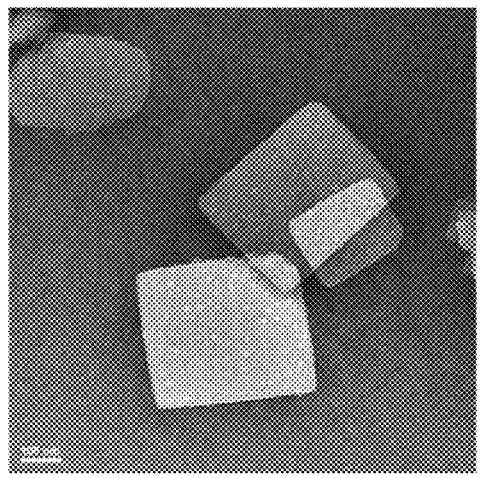
Figure 34:
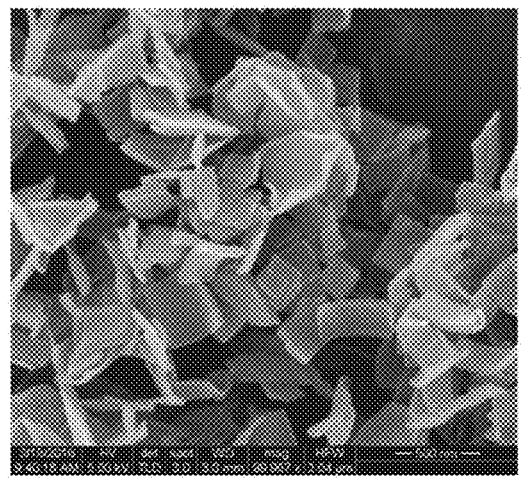

FIG. 34. TEM and SEM images of DTX/Cim-F-alb

FIG. 35. Dissolution of DTX/Cim-F-alb in FIG. 35A 10% FBS FIG. 35B 50% FBS using Dynamic Light Scattering method (DLS). Derived count rate of nanocrystals incubated at different concentrations in each media was measured over 24 hrs. 10% or 50% FBS incubated at same condition was used as a blank. DTX/Cim-F-alb remained as nanocrystal at concentration >5 µg/ml in 10% FBS and >10 µg/ml in 50% FBS.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In response to the unmet need, novel compositions of carrier-free nanoparticles and novel methods of making carrier-free nanoparticles are disclosed herein.

To develop a carrier-free nanoparticle formulation of PTX with good circulation stability, PTX NC (Cim-F-alb) were produced by crystallizing PTX in a medium containing Pluronic F127 and stabilizing the NC surface with native albumin. Cim-F-alb had a smaller size and native albumin than other NC produced by a different crystallization method or surfactant. The small size and native conformation of surface-bound albumin resulted in reduced uptake by J774A.1 macrophages and increased uptake by SPARC-positive B16F10 melanoma cells. Cim-F-alb outperformed Abraxane in a mouse model of B16-F10 melanoma. Without being bound by any theory, the in vitro dissolution profile in undiluted serum suggests that the superior performance of Cim-F-alb is likely due to the circulation stability of the nanoparticles, which leads to their preferential tumor accumulation and retention.

In at least one embodiment, slowly dissolving nanocrystals may be modified with a protective surface agent that is configured to enhance the tumor distribution of a particular nanocrystal in a given environment. Therefore, in at least one embodiment, the protective surface agent may be a protein, for example albumin.

Further, in at least one embodiment, crystallization can be induced using a surfactant. The appropriate surfactant is one that is suitable and configured for aiding the crystallization in a given system and environment. In an embodiment, the crystallization can be induced in a matrix of a surfactant, for example Pluronic F127.

As demonstrative of the methods described herein, to overcome the limitations in reducing particle size with conventional bottom-up methods, we induced crystallization in a matrix of a surfactant, such as Pluronic F127. The presence of polymer matrix limits the growth of crystals; thus, this method can form relatively small particle size (<200 nm). The incipient nanocrystals (iCim) are harvested by sonication and hydration and stabilized with surface modifiers with higher affinity for nanocrystals such as albumin or polysaccharide derivatives. Pluronic F127 is replaced by the surface modifiers and mostly absent in the final product. Due to the small size and the lack of polymeric surfactant, it may provide faster dissolution of a drug and greater safety than other nanocrystal formulations.

Anticancer drugs are formulated in various types of nanoparticles, based on the premise that small particles will gain a selective access to tumors via hyperpermeable vasculature [1]. However, their clinical development has been tedious because of the limitations in physicochemical properties of nanoparticles [2] and the complexity of human cancer that have been poorly simulated in preclinical models [3-5]. Among physicochemical challenges, low drug loading efficiency and poor circulation stability are critical issues that can overshadow most benefits of nanoparticles. With low drug loading efficiency (typically <20 wt % of total nanoparticle mass [2]), nanoparticles bring a large amount of carrier materials in addition to the drug. Although the carrier materials are judiciously selected and tested for safety, their biological activities and long term effects are not always predicted in the early stage of development, where the outcomes are monitored with a limited number of doses over a short period of time. Accumulated over repeated administrations, slowly degrading (or non-degrading) carrier materials become an increasing biological burden to patients [6, 7]. Moreover, the high fraction of carrier materials increases the total mass to administer, thus increasing the injection volume and/or the concentration of the nanoparticles such that the volume and concentration of a treatment become dose limiting factors [2, 8]. Concentrated nanoparticles can undergo irreversible aggregation and undue clearance by the mononuclear phagocyte system (MPS), negatively affecting the bioavailability of the treatment. Another prevalent but frequently overlooked challenge is the unstable drug retention in nanoparticles during circulation. Many nanoparticles retain drugs stably in buffered saline but release them almost instantaneously when exposed to physiological media containing proteins and lipids [9]. Nanoparticles losing the payload in circulation are unlikely to provide benefits over conventional solution formulations, no matter how stable they are in buffered saline and what they are capable of in cell models.

In recognition of the problems related to low drug loading efficiency, a selected group of drugs have been formulated into small crystalline particles called nanocrystals (NC). Poorly water-soluble drugs such as paclitaxel (PTX) or docetaxel tend to form solid particles in water. With optimal processing methods and surface stabilizers, these poorly-soluble drugs may be made into NC with a size ranging from 100 to 300 nm. The processing methods may be "top-down" (breaking down large particles with high shear stress), "bottom-up" (inducing nucleation of drug molecules by solvent and/or temperature conditions), or combinations of the two [10]. Since NC are produced from the drug itself and a small quantity of surface stabilizers, the drug content in NC is close to 100 wt % [10]. Depending on the lattice energy between drug molecules, the NC can remain quite stable in aqueous media and serve as nanoparticles [11].

As nanoparticles with high drug loading efficiency (i.e., drug content), NC have drawn increasing interest in the field of nanomedicine as a way of delivering poorly water-soluble anticancer drugs. For example, PTX NC were produced by an anti-solvent and reduced temperature and tested in a colon cancer xenograft murine model [12]. Another type of PTX NC were produced by transforming an amorphous mixture of PTX and Pluronic F127 into crystalline particles and tested in two tumor models [13]. As NC were mostly distributed in the MPS organs leaving little drug in circulation [12, 14, 15], the NC were further modified with polyethylene glycol (PEG) by forming NC together with PEGylated PTX [16] or a crosslinkable polymeric amphiphile containing PEG [17]. Recently, iron-tannic acid complex was used to coat PTX nanoassemblies with an intention to reduce their MPS uptake [18]. However, none of these NC or self-assemblies showed better antitumor effects than commercial PTX formulations such as Taxol (surfactant-solubilized PTX) or Abraxane (albumin-bound PTX) at equivalent doses [12, 13, 18, 19], making their therapeutic benefits a moot point.

We hypothesize that the relative inefficiency of NC may be due to the limitations in size control and suboptimal surface properties. With traditional top-down or bottom-up methods, it is difficult to reduce the particle size to below 200 nm, the upper size limit for preferential extravasation through the leaky tumor vasculature [20]. In addition, bare NC with hydrophobic surfaces prone to non-specific protein adsorption are readily subject to MPS uptake [21]. PEG or other hydrophilic 'stealth' surface help reduce the MPS uptake of NC, but they can interfere with the retention and intended cellular interactions after NC distribution in tumors [22]. To address these challenges, we use the NC preparation method introduced by Liu et al [13] and further modify the NC surface with serum albumin. By inducing crystallization in the presence of a surfactant intimately associated with the drug, this preparation method creates NC with a size less than 200 nm [13]. Albumin is the most abundant protein in plasma involved in transendothelial transport of nutrients and drugs [23, 24]. As a native protein with a long circulation half-life, albumin bound to hydrophobic nanoparticles can prevent their opsonization and phagocytosis [25, 26]. Moreover, many tumors have a high demand for albumin as a major source of energy and nutrients [27], and, therefore, an increased capacity to take up albumin. Albumin can extravasate not only by paracellular pathway but also via transcellular pathway that involves gp60 (albondin) [23]. Once in tumors, albumin can bind to SPARC (secreted protein acidic and rich in cysteine) expressed in various cancer cells and tumor interstitium [28]. Based on these features, we expect that albumin modification will help NC to avoid MPS uptake, translocate across the tumor endothelium, and stay in tumors.

In this study, we produce the mentioned NC and two additional NC with different sizes and incipient surfaces for albumin binding and compare their cellular interactions to investigate the effect of the size and the status of surface-bound albumin. The best NC form is compared with Abraxane with respect to the dissolution behavior and in vivo antitumor activities. Our results show that small size of NC and native status of albumin lead to favorable cellular interactions and help the NC to outperform Abraxane in a SPARC-positive B16F10 melanoma model.

Materials and Methods

Materials

PTX was a gift of Samyang Biopharm (Seoul, Korea). Pluronic F127 (F127) was a gift from BASF (New York, N.Y., USA). Abraxane was obtained from Celgene Corporation (Summit, N.J., USA). Human serum albumin (≥96% agarose gel electrophoresis) and hexadecyltrimethylammonium bromide (CTAB) were purchased from Sigma-Aldrich (St. Louis, Mo., USA). Reagents for sodium dodecyl sulfate polyacrylamide gel electrophoresis (SDS-PAGE) were purchased from Bio-Rad (Hercules, Calif., USA). Terminal deoxynucleotidyl transferase dUTP nick end labeling kit (DeadEnd Fluorometric TUNEL System) was purchased from Promega (Madison, Wis., USA). All other reagents were purchased from Sigma-Aldrich (St. Louis, Mo., USA).

Nanocrystal Production

Figure 1:
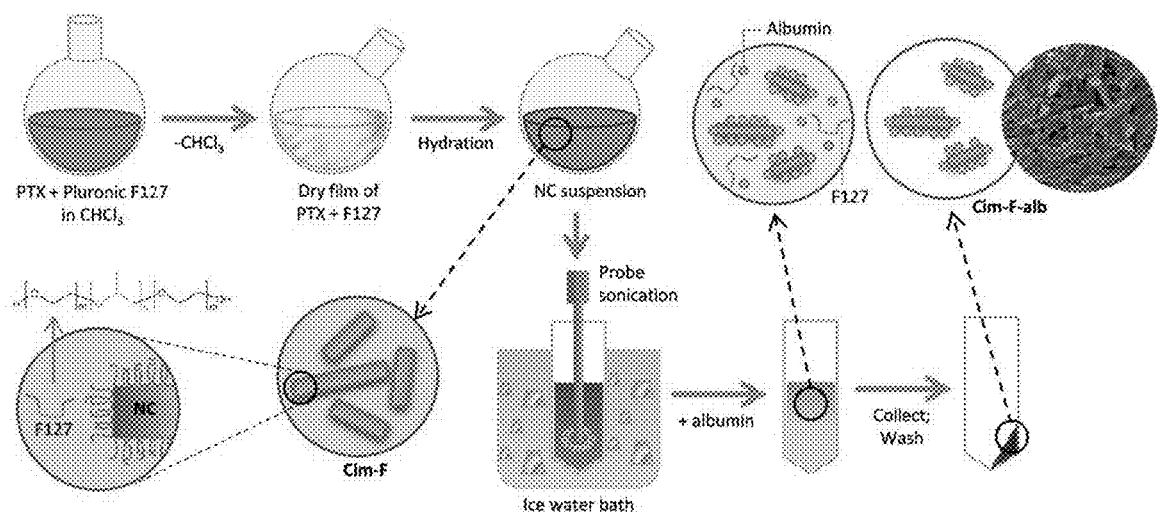
FIG. 1. Schematic description of Cim-F-alb preparation.

NC were prepared in two steps: crystallization in surfactant-containing medium, followed by surface coating with albumin (FIG. 1). The first step followed the method described by Liu et al [13] with modification. Briefly, a mixture of PTX and surfactant (6 mg PTX and 24 mg Pluronic F127 or 2.4 mg of CTAB) was fully dissolved in 3 mL of chloroform in a round-bottom flask. Chloroform was evaporated with a rotary evaporator at 40° C. for 10 min to form a thin film on the wall of the flask. Six milliliters of DI water was added to the film at room temperature. The formed incipient NC were called Cim-F (Crystallized in medium containing F127) and Cim-C(Crystallized in medium containing CTAB), according to the type of surfactants included in the film. The PTX/surfactant film was hydrated for 5 sec to 15 min with bath sonication, and the hydrated suspension was probe-sonicated in an ice-water bath for 15 min with a power level of 40% and a 1:1 duty cycle every 2 sec. In the second step, the NC were stabilized with albumin. Four milligrams of albumin was added to 1 mL of NC suspension (equivalent (eq.) to 1 mg PTX) and incubated at room temperature for 24 h on a rotating rocker. The NC suspension was centrifuged at 135,700 rcf for 10 min at 4° C. to remove excess surfactant and unadsorbed albumin. The pellet was re-suspended in water and collected by centrifugation at 135,700 rcf for 10 min at 4° C. The formed NC were called Cim-F-alb (Cim-F stabilized with albumin) and Cim-C-alb (Cim-C stabilized with albumin). For confocal microscopy, Cim-F-alb was labeled with Rhodamine B (Cim*-F-alb) by adding 0.1 mg/mL of aqueous rhodamine B solution in the film hydration step. The amount of incorporated rhodamine B was measured based on fluorescence intensity ($\lambda_{ex}/\lambda_{em}$: 540 nm/625 nm) of Cim*-F-alb dissolved in acetonitrile (ACN). Alternatively, Cim-F-alb labeled with Oregon green (Cim#-F-alb) was produced by replacing a small fraction of PTX with Oregon green-conjugated PTX.

For comparison, NC were also prepared by the antisolvent and temperature-induced crystallization described in the literature [29]. Briefly, 1 mL of 4 mg/mL PTX/ethanol solution was added to 20 mL of DI water and stirred for 10 min in a round-bottom flask immersed in an ice water-filled sonication bath. Ethanol was removed by 10 min rotary evaporation at 40° C. NC were collected on a polycarbonate membrane filter with an average pore size of 100 nm and retrieved in DI water by 1 min bath sonication. The formed NC were called PNC. To form an albumin-coated PNC (PNC-alb), albumin was added to PNC suspension (equivalent to 1 mg/mL PTX) to make 4 mg/mL and incubated at room temperature for 24 h on a rocking shaker. PNC-alb was washed in the same way as above.

Nanocrystal Characterization

Particle Size

The particle size of NC was measured in sodium phosphate buffer (1 mM, pH 7.4) with a Zetasizer Nano-ZS90 (Malvern instruments, Westborough, Mass., USA). The particle size was measured at each step of preparation (hydration, albumin coating, and washing).

Morphology

The morphology of NC was examined with a Phillips CM-100 transmission electron microscopy (Hillsboro, Oreg., USA). Samples were mounted on a 400-mesh Cu grid with Formvar/carbon supporting film and stained with 2% phosphotungstic acid. Images were captured with a SIA L3-C2 megapixel CCD camera (Scientific Instruments and Application, Duluth, Ga.).

X-Ray Powder Diffraction (XRPD)

Cim-F-alb and its intermediate were analyzed with a Rigaku Smartlab™ diffractometer (Rigaku Americas, Tex., USA) with a Cu-Kα radiation source and a highly sensitive D/tex ultra detector. The powders were placed in glass sample holders, and powder patterns were obtained from 5 to 40° 20 at a scan speed of 4°/min and a step size of 0.02°. The voltage and current used were 40 kV and 44 mA, respectively.

PTX Content

The PTX content in NC was determined by HPLC. NC with a premeasured mass were dissolved in a 50:50 mixture of ACN and water at a concentration of 30-60 μg/mL and filtered with 0.45 μm syringe filter prior to analysis. HPLC was performed with an Agilent 1100 HPLC system (Palo Alto, Calif.), equipped with Ascentis C18 column (25 cm×4.6 mm, particle size: 5 μm). The mobile phase was a 50:50 mixture of water and ACN and run at 1 mL/min. PTX was detected by a UV detector at a wavelength of 227 nm.

Albumin Content and Status

The albumin content in NC was determined with SDS-PAGE. NC with a premeasured mass or standard albumin solutions were mixed with 4× Laemmli sample buffer and heated at 95° C. for 5 min. The samples were resolved in a 12% polyacrylamide gel. The gel was stained with QC Colloidal Coomassie Stain (Bio-Rad, Hercules, Calif., USA) and imaged with Azure C300 (Dublin, Calif., USA). The albumin bands were quantified by densitometry function of the AzureSpot Analysis Software (Dublin, Calif., USA). The albumin content was determined by comparing the band intensities of NC samples and standard albumin solutions.

The status of the NC-bound albumin was analyzed by pulse proteolysis [30]. PNC-alb, Cim-C-alb, and Cim-F-alb (eq. to 0.2 mg/mL albumin) were treated with 0.2 mg/mL of thermolysin in HEPES buffer (pH 7.4, 20 mM) containing 100 mM NaCl and 10 mM $CaCl_2$. After 5 min incubation at room temperature, 5 μL of 50 mM EDTA was added to a 15 μL aliquot to quench proteolysis. For the control, NC were treated the same without thermolysin. The treated NC was mixed with 4× Laemmli sample buffer and heated at 95° C. for 5 min. The samples were resolved in 15% polyacrylamide gel and detected with QC Colloidal Coomassie Stain. The protein bands were imaged with Azure C300 to analyze the extent of proteolysis of surface-bound albumin. The percent digestion was calculated as (1−the band intensity of albumin after proteolysis/the band intensity of albumin prior to proteolysis)×100.

The functional status of NC-bound albumin was estimated based on its esterase activity [31]. PNC-alb, Cim-C-alb, and Cim-F-alb (eq. to 0.5 mg/mL albumin) in sodium phosphate buffer (pH 7.4, 0.2 M) was incubated with 100 μM of p-nitrophenyl acetate (pNPA) at room temperature. Immediately and 60 min after the addition of pNPA, a supernatant was separated from the NC suspension by centrifugation and read at 405 nm to quantify p-nitrophenol (product of pNPA hydrolysis). The amount of active albumin was calculated based on the rate of pNPA hydrolysis. The percent active albumin was calculated as the amount of active albumin divided by the amount of total albumin determined with SDS-PAGE.

Cellular Uptake of NC

J774A.1 mouse macrophage cells (ATCC, Manassas, Va., USA) and B16F10 mouse melanoma cells (ATCC, Manassas, Va., USA) were grown in DMEM medium containing 10% fetal bovine serum (FBS) and penicillin (100 IU/mL) and streptomycin (100 μg/mL). Cells were seeded in a 6 well plate at a density of 100,000 cells per well. After overnight incubation, the cell culture medium was replaced with fresh medium, to which 100 μL of PNC-alb, Cim-C-alb, or Cim-F-alb in PBS was added to provide the final concentration equivalent to 30 μg/mL PTX. After incubation with the treatments for 30 min (J774A.1) or 3 h (B16F10), cells were washed with PBS two times to remove unbound NC.

The cells in each well were then collected in 1 mL of PBS. A 30 µL fraction of the cell suspension was analyzed with a flow cytometer to determine the cell count. The rest was analyzed to determine PTX taken up by the cells. Briefly, the cell pellet was lysed with 3 cycles of freezing and thawing, followed by probe sonication. The cell lysate was extracted with ethyl acetate, and the content of PTX in the ethyl acetate phase was analyzed with HPLC. Carbamazepine (CBZ) was used as an internal standard during the extraction.

For J774A.1 macrophages, the same experiment was repeated at 4° C. or after pretreatment with polyinosinic acid. When the experiment was performed at 4° C., the macrophages were equilibrated at 4° C. for 30 min prior to the NC treatment. When polyinosinic acid was used, the macrophages were preincubated with 100 µg/mL of polyinosinic acid in serum-free medium for 30 min, washed once with PBS, and treated with NC in serum-free medium for 30 min. Intracellular PTX content was determined as described above. For B16F10 cells, the same experiment was repeated with and without albumin (5-50 mg/mL) in serum-free medium.

Cytotoxicity

Cytotoxicity of NC after 3 h Treatment

Cytotoxicity of NC was tested with B16F10 cells. B16F10 cells were grown in RPMI-1640 or DMEM medium supplemented with 10% FBS, penicillin (100 IU/mL) and streptomycin (100 µg/mL). B16F10 cells grown in RPMI-1640 were seeded in a 96 well plate at a density of 10,000 cells per well. After overnight incubation, the culture medium was replaced with a fresh cell culture medium, to which PNC-alb, Cim-C-alb, or Cim-F-alb were added to provide the final concentration eq. to 30 µg/mL PTX. After 3 h incubation, cells were washed with PBS twice to remove NC, followed by additional incubation for 21 h in NC-free medium. The cell viability was determined by the MTT (3-(4,5-dimethylthiazol-2-yl)-2,5-diphenyltetrazolium bromide) assay. Cells were treated with 75 µg of MTT and incubated for 3.5 h. The formazan crystals were dissolved in stop/solubilization solution (50% DMF, 20% SDS, pH 5) and quantified with a SpectraMax M3 microplate reader (Molecular Devices, CA, USA) at the wavelength of 562 nm. The measured absorbance was normalized to the absorbance of control cells that did not receive treatments.

B16F10 cells grown in DMEM medium was tested with propidium iodide (PI) staining due to the production of melanin [32], which interferes with colorimetric assay. B16F10 cells were seeded in a 6 well plate at a density of 100,000 cells per well. After overnight incubation, the medium was replaced with fresh medium, to which 100 µL of PNC-alb, Cim-C-alb, or Cim-F-alb in PBS was added to provide the final concentration eq. to 30 µg/mL PTX. After incubation with NC for 3 h, cells were washed with PBS two times to remove NC, followed by additional incubation for 21 h in NC-free medium. Then, B16F10 cells were trypsinized and stained with PI (1 µg/mL) for 15 min in dark at room temperature. The cells were centrifuged at 300 g for 5 minutes to remove extra PI dye and reconstituted in PBS for flow cytometry (Accuri C6, BD Biosciences, San Jose, Calif.). At least 15,000 gated events were acquired, and FL-2 channel was monitored to determine the population of PI-stained cells.

$IC_{50}$ Determination

Cytotoxicity of Cim-F-alb was tested with B16F10 cells and SKOV-3 human ovarian cancer cells (ATCC, Manassas, Va., USA) over a range of PTX concentrations. SKOV-3 cells were grown in RPMI-1640 medium containing 10% FBS and penicillin (100 IU/mL) and streptomycin (100 µg/mL). Both cells were treated with Cim-F-alb for 24 h, followed by post-treatment incubation in NC-free medium for 12-48 h. Free PTX and Abraxane were tested in the same manner for comparison. Cim-F-alb and Abraxane were directly reconstituted in PBS and serially diluted by a factor of 10. Free PTX solution was prepared as PTX stock solution in 50% DMSO at a concentration of 1 mg/mL and diluted in PBS. The maximum possible concentration of DMSO in the medium was 5% v/v. SKOV-3 cells and B16F10 cells grown in RPMI-1640 were tested with the MTT assay, and B16F10 cells grown in DMEM were tested with PI staining and flow cytometry. $IC_{50}$ was calculated with GraphPad Prism 6 (La Jolla, Calif., USA).

Intracellular Localization of Cim-F-alb

Cim*-F-alb uptake by B16F10 cells was observed with confocal microscopy. B16F10 cells were seeded in a 35 mm dish with a glass window (MatTek) at a density of 50,000 cells per dish. After 24 h, the medium was replaced with fresh medium, and the cells were incubated with LysoTracker Green DND-26 (25 nM) for 30 min. After washing, cells were incubated with Cim*-F-alb or Cim#-F-alb (30 µg/mL PTX eq.) or free rhodamine B solution (0.3 µg/mL) for 30 min in complete medium. Following two washes with PBS, the cells were fixed with 4% paraformaldehyde in PBS for 10 min. After 5 min nucleus staining with Hoechst 33342 (2 µg/mL), the fixed cells were imaged with a Nikon A1R confocal microscope. Hoechst and LysoTracker Greeen DND-26 were detected with $\lambda_{ex}/\lambda_{em}$ of 407 nm/425-475 nm and 488 nm/500-550 nm, respectively. Cim*-F-alb or free Rhodamine B was detected with $\lambda_{ex}/\lambda_{em}$ of 561 nm/570-620 nm. Cim#-F-alb was detected with $\lambda_{ex}/\lambda_{em}$ of 488 nm/500-550 nm. The same experiment was repeated at 4° C. Prior to Cim*-F-alb treatment, the cells were equilibrated at 4° C. for 30 min following LysoTracker labeling.

Dissolution of Cim-F-alb in PBS and FBS

Based on the linear relationship between the number of particles and light scattering intensity, the derived count rate (i.e., absolute light scattering) was monitored as a measure of particle dissolution in PBS or undiluted FBS. Cim-F-alb and Abraxane equivalent to PTX 25-100 µg/mL were incubated in PBS or FBS at 37° C. for 24 h with periodical measurements of their derived count rates using a Zetasizer Nano-Z590. The FBS suspension was sampled at 6 h to quantify dissolved PTX by that time. A supernatant was separated from the sample by 10 min centrifugation at 135,700 rcf and analyzed as described in 2.4.

Dissolution of Cim-F-alb and Abraxane was monitored by measuring changes in light scattering intensities over time. Briefly, 10 µL of particle suspensions equivalent to 2 µg or 30 µg of PTX was added to 990 µL of FBS or PBS containing 0.2% Tween80 (PBST) to make the final volume 1 mL. After gentle mixing, a series of measurements were performed at 25° C. using a Zetasizer Nano-ZS90. Each measurement was done for 2 runs at 2 sec, at the measurement position of 4.65 mm and with an attenuator setting of 10.

In Vivo Activity of Cim-F-alb

Anti-Tumor Activity

All animal procedures were approved by Purdue Animal Care and Use Committee, in conformity with the NIH guidelines for the care and use of laboratory animals. Eight to ten week old male C57BL/6 mice were obtained from Envigo (Indianapolis, Ind., USA) and acclimatized for 1 week prior to the procedure. Each mouse received a subcutaneous injection of $10^6$ B16F10 melanoma cells in the upper flank of the right hind leg. When the tumor was palpable (12 days after tumor cell inoculation), the animals were randomly assigned to 3 groups (n=6 for PBS and Abraxane-treated group, n=7 for Cim-F-alb group) and treated with 4 tail vein injections of PBS, Abraxane, or Cim-F-alb (equivalent to 15 mg/kg of PTX in 100 µL per injection) at 3-day interval. Abraxane and Cim-F-alb were prepared in sterile PBS freshly on the day of treatment. Tumor volume and body weights were monitored every day. The length (L) and width (W) of each tumor were measured with a digital caliper, and the volume (V) was calculated according to the modified ellipsoid formula: $V=(L \times W^2)/2$. Specific growth rate of a tumor was calculated as $\Delta \log V/\Delta t$ (t: time in days) [33]. One day after the last injection, mice were sacrificed for the tumor tissue analysis. The excised tumors were fixed in 10% neutral buffered formalin solution or frozen at −80° C. until analysis. Animals losing weight in excess of 20% body weight or with tumors reaching >10% body weight were humanely euthanized prior to the end of the study.

PTX Content in Tumor

The frozen tumors were homogenized in PBS using a Tissue Master 125 homogenizer (Omni International). One milliliter of the homogenate was mixed with 3 mL of ethyl acetate with 35 µg of CBZ as an internal standard and rotated for 1 h for PTX extraction. After centrifugation at 3,724 rcf for 10 min, 2.8 mL of ethyl acetate layer was evaporated and dissolved in a 1:1 mixture of ACN/water for HPLC analysis.

TUNEL Assay of Tumor Sections

The fixed tumor tissues were embedded in paraffin, sectioned, and mounted on a glass slide for TUNEL assay (DeadEnd Fluorometric TUNEL system; Promega). Images were taken with a Nikon A1R confocal microscope. Two randomly selected fields per tissue were analyzed with ImageJ (National Institutes of Health, Bethesda, Md.) to count apoptotic cells and nuclei. Percent apoptotic cells were calculated as the ratio of the number of apoptotic cells to the number of the nuclei.

Statistical Analysis

All statistical analysis was performed with GraphPad Prism 6. All in vitro data were analyzed with one-way or two-way ANOVA test to determine the difference of means among groups, followed by Tukey's or Sidak's multiple comparisons test. In vivo data were analyzed with one-way ANOVA, followed by Tukey's multiple comparison test unless specified otherwise. A value of $p<0.05$ was considered statistically significant.

Determination of Maximum Tolerated Dose (MTD) of Cim-F-alb

Male C57BL/6 mice were obtained from Envigo (Indianapolis, Ind., USA). Health mice received different doses of Cim-F-alb (15 mg/kg, 30 mg/kg, 60 mg/kg, and 90 mg/kg PTX) every 3 days five times via tail vein injection (n=3 for each dose level, except 15 mg/kg PTX group, which was n=1). The body weight change was monitored every day with body weight loss in excess of 20% body weight considered a human endpoint.

In Vivo Antitumor Activity Evaluation at MTD

Tumor-bearing mice were prepared as described in Section 2.8 of _JCR manuscript and treated with Cim-F-alb at the dose of PTX 30 mg/kg q3d×5 times. Changes in body weight and tumor size were monitored every day.

PK/BD Evaluation of Cim-F-alb

Cim-F-alb or Abraxane equivalent to 30 mg/kg PTX was administered to C57BL/6 mice bearing subcutaneous B16F10 tumors by tail vein injection. At predetermined time points (0.5, 1, 3, 6, 12, and 24 hr post-injection), mice were euthanized by cardiac puncture, and major organs (heart, lung, liver, spleen, and kidney) and tumor tissue were collected for analysis (n=3 at each time point per group). PTX extracted from homogenized organs and blood plasma was analyzed by LC-MS.

Application of Cim-F-alb Technique to Carfilzomib (CFZ)

CFZ NCs were prepared in a similar way as Cim-F-alb. Six milligrams of CFZ and 48 mg of F127 were dissolved in 3 mL of chloroform in a round-bottom flask. Chloroform was evaporated with a rotary evaporator at 40° C. for 10 min to form a thin film on the wall of the flask. The film was hydrated for 10 s with bath sonication, and the suspension was probe-sonicated in an ice-water bath for 15 min with a power level of 40% and a 1:1 duty cycle every 2 s. Then, the suspension was incubated with albumin (4 mg of albumin to 1 mg PTX equivalent) for 24 h on a rotating rocker. The formed NC (CFZ/Cim-F-alb) suspension was centrifuged at 135,700 rcf for 10 min at 4° C. to remove excess surfactant and unadsorbed albumin.

The CFZ content in CFZ/Cim-F-alb was analyzed by HPLC, and albumin was quantified by SDS-PAGE. To test dissolution of CFZ/Cim-F-alb in PBS and FBS, the NC ranging from 10 µg/mL to 100 µg/mL was incubated in PBS or FBS at 37° C., and the derived count rate was monitored over 24 h.

Application of Cim-F-alb Technique to Docetaxel (DTX)

DTX NCs were prepared and analyzed in a similar way as Cim-F-Alb discussed above.

Results and Discussion

Preparation of PNC-alb, Cim-C-alb, and Cim-F-alb

Albumin-coated PTX NC were prepared in two steps: First, incipient NC were prepared by inducing PTX crystallization with an anti-solvent and low temperature [29] or hydrating a dry film of PTX/surfactant mixture [13]. Subsequently, albumin was added to the NC suspension and incubated with the NC to let the protein adsorb on the NC surface.

Figure 2:
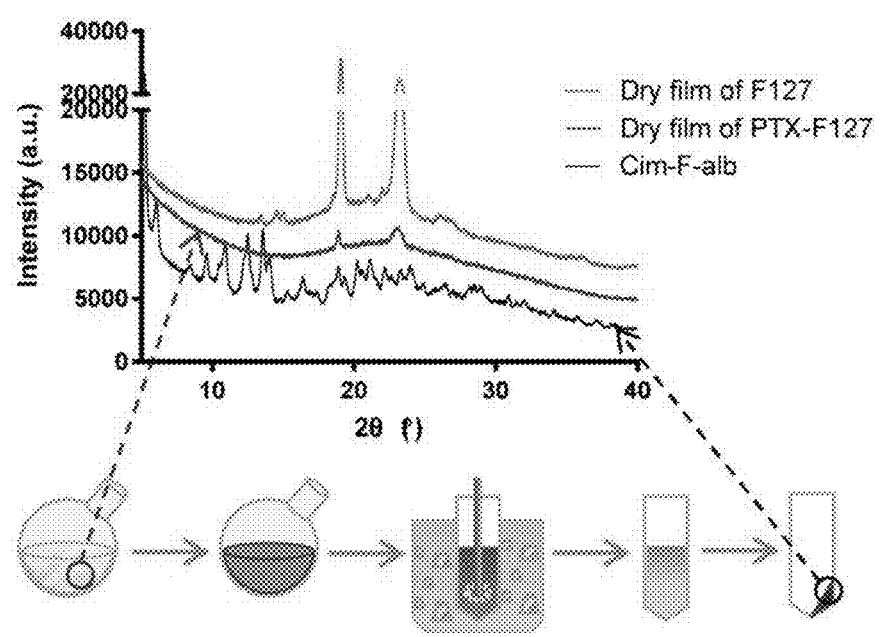
FIG. 2. X-ray powder diffraction patterns of a dry film of F127, a dry film of PTX and F127 mixture, and Cim-F-alb.

The incipient NC prepared by the anti-solvent and low-temperature induced crystallization (PNC) showed a z-average of 321.7±34.1 nm. The NC formed from a dry film of PTX-surfactant mixture (Cim-F and Cim-C) were substantially smaller: 154.8±33.1 nm (Cim-F) and 237.8±18.7 nm (Cim-C). The relatively small size is attributable to the surfactant present in the crystallization medium. In a dry film, PTX and F127 form an amorphous mixture making contacts at a molecular level as shown by the XRPD pattern (FIG. 2). PTX transforms to crystalline particles through the hydration and sonication step (FIG. 2). During hydration, F127, a triblock copolymer of poly(ethylene oxide)-poly (propylene oxide)-poly(ethylene oxide) (PEO-PPO-PEO), starts to dissolve and adsorb to the NC surface via the hydrophobic PPO block, exposing the hydrophilic PEO domains to water. Present at the interface between the incipient NC and the medium, F127 effectively suppresses the crystal growth and their agglomeration. Consistently, Liu et al observed the formation of large crystals in the absence of F127, ascertaining the critical role of F127 in forming small NC [13]. As a surfactant, CTAB is considered to have a similar function.

Figure 3:
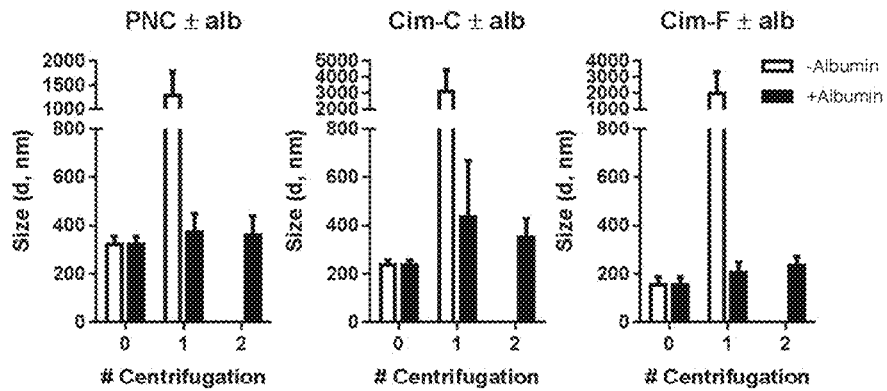
FIG. 3.
Figure 3:
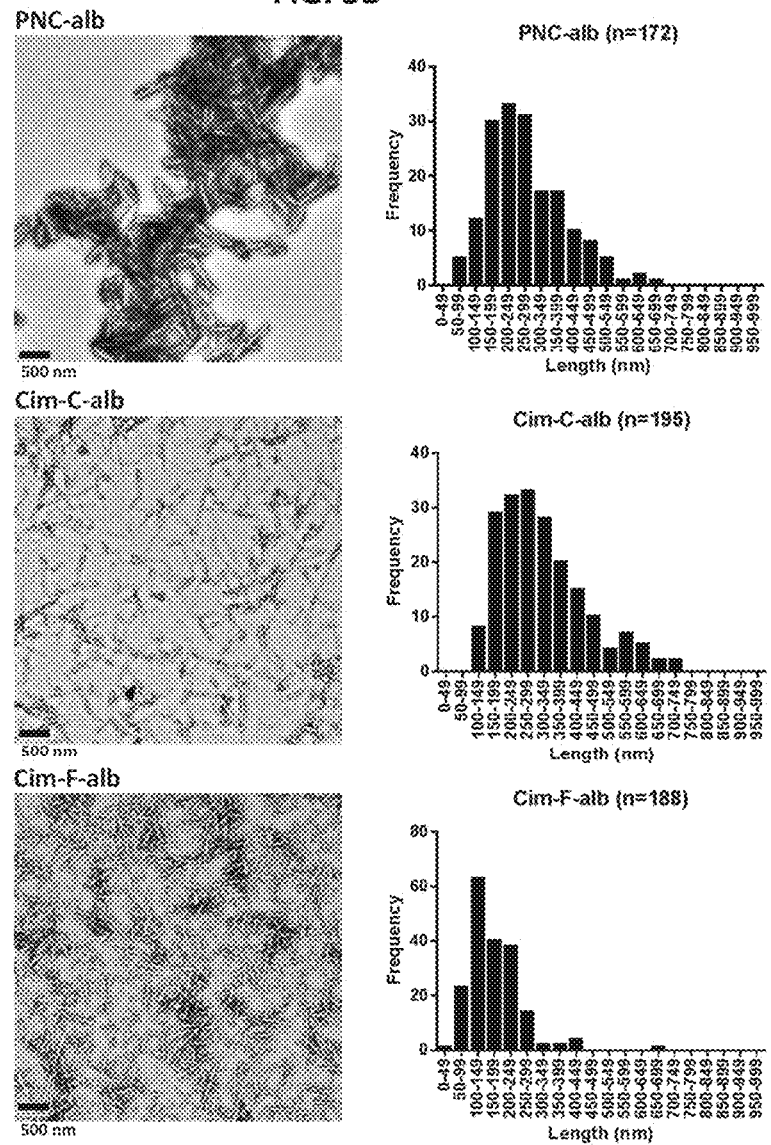

The second step involved albumin coating of the NC surface and the removal of excess albumin and surfactants (for Cim-F-alb and Cim-C-alb) by repeated centrifugation and resuspension in water. Excess surfactants were removed for potential safety issues. Although F127 is generally considered a nontoxic excipient and has been used as an emulsifying agent in parenteral products [34], studies have reported that F127 could produce hypercholesterolemia in mice after single intraperitoneal (IP) injection at a dose of 500 mg/kg [35] and induce reversible changes in the renal filtration capacity in rats after IP administration at 1000 mg/kg [36]. CTAB is also considered nontoxic, but free CTAB was reported to be cytotoxic in HT-29 colon cancer cells [37], HeLa cervical cancer cells [38], and K562 chronic myelogenous leukemia cells [39]. In the absence of excess surfactants, the surface-bound albumin helped to prevent agglomeration of NC during the purification step. Without albumin, the incipient particles (PNC, Cim-F, and Cim-C) formed micrometer-scale agglomerates upon centrifugation, which were not redispersed to the original size (FIG. 3a). On the other hand, NC coated with albumin withstood centrifugation better and maintained their submicron sizes. After the final step, Cim-F-alb had the smallest z-average (235.6±36.5 nm), and Cim-C-alb and PNC-alb were similar (351.9±75.3 nm and 358.9±79.6 nm) (FIG. 3a).

Figure 12:
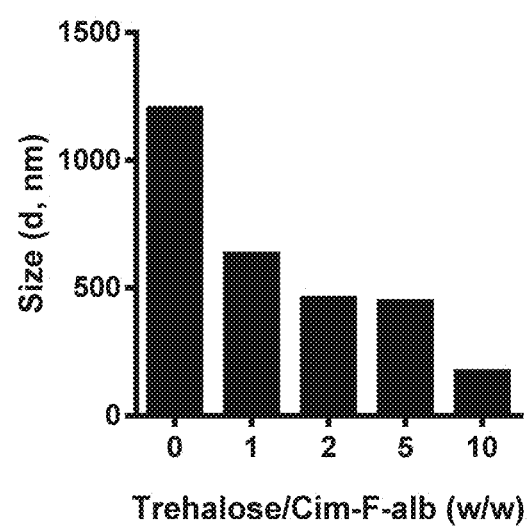
FIG. 12. Particle size of Cim-F-alb freeze dried with different trehalose/Cim-F-alb w/w ratio and reconstituted in water.

The size of Cim-F-alb could be further reduced by adjusting the duration of hydration. Compared to 15 min, 5 sec hydration produced smaller particles with a z-average of 196.7±34.6 nm (FIG. 11). Reflecting the smaller size, Cim-F-alb formed by 5 sec hydration showed accelerated dissolution in PBS containing 0.2% Tween 80 (PBST) as compared to those formed by 15 min hydration (FIG. 11). The dependence of particle size on the hydration time indicates that NC grew during the hydration step whereas the subsequent sonication step helped perturb the NC growth. Cim-F-alb could be lyophilized and reconstituted to the original size with trehalose as a lyoprotectant (FIG. 12).

Morphology and Composition of PNC-alb, Cim-C-alb, and Cim-F-alb

All NC showed a long rod shape, but their size and aspect ratio were slightly different according to the media in which the incipient NC were prepared (FIG. 3b). PNC-alb showed a rod shape with a length of 254.7±119 nm and a width of 76.5±21 nm (n=172 with ImageJ). Cim-C-alb and Cim-F-alb showed a higher aspect ratio with smaller widths. Cim-C-alb had an average length of 342.5 nm±132 nm and a width of 33.5±7 nm (n=195), while Cim-F-alb had a length of 198.4±80 nm and a width of 35.8±6 nm (n=188). The rod shape is expected to be beneficial for systemic drug delivery as it helps avoid the particle uptake by the MPS [40]. The prismatic morphology suggests the crystalline nature of NC, which was consistent with the result of XRPD (FIG. 2). Cim-F-alb displayed sharp peaks typical of crystalline solids, similar to PNC [29].

The PTX contents in PNC-alb, Cim-C-alb, and Cim-F-alb were 88.5±4.2 wt % (n=4), 79.2±5.1 wt % (n=4), 88.7±2.5 wt % (n=4), respectively. The albumin contents were 7.6±1.4 wt % (PNC-alb), 14.8±0.7 wt % (Cim-C-alb), and 9.7±0.9 wt % (Cim-F-alb) (Supporting FIG. 3). The amount of remaining F127 and CTAB were not directly measured, but according to the mass balance their contents were estimated to be 1-6 wt %. While albumin is an acidic protein with an isoelectric point of pH 4.7, the amount of surface-bound albumin did not directly correlate with the zeta potential of the albumin-bound NC (FIG. 13). PNC-alb and Cim-C-alb had similar zeta potentials despite the significant difference in the albumin contents. Cim-F-alb was not as negatively charged as PNC-alb, even though the albumin contents were comparable. Based on this observation, we hypothesized that the conformation and arrangement of surface-bound albumin might be different depending on the platform to which albumin was binding (i.e., hydrophobic surface of PNC-alb, cationic surface of Cim-C, and hydrophilic surface of Cim-F). To test this, we investigated the status of albumin bound to NC.

Evaluation of the Status of Albumin Bound on PNC-alb, Cim-C-alb, and Cim-F-alb

Figure 14:
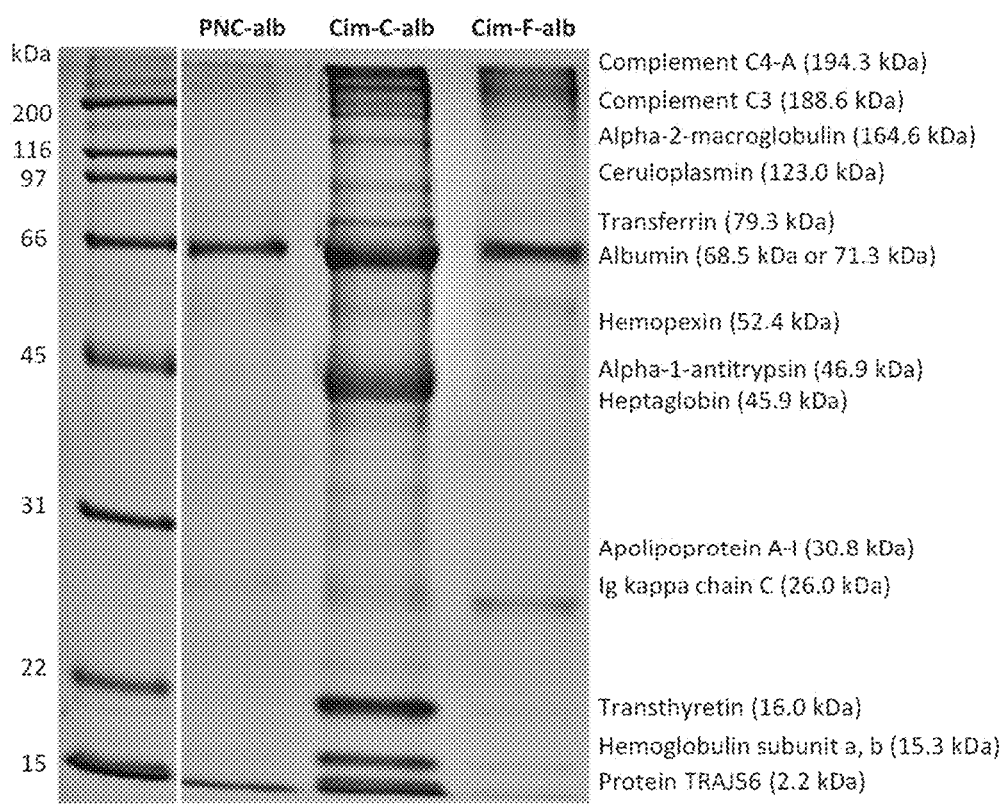
FIG. 14. Proteins bound to NC. The NC were analyzed by SDS-PAGE as described in Section 2.3.5, and the protein bands were identified by LC-MS/MS. Briefly, the Coomassie stained bands were excised from the gel and destained by washing with a 50:50 mixture of 25 mM ammonium bicarbonate (ABC; pH 8.5) and ACN for 4 times. The gel was dried with vacuum centrifuge and treated with 10 mM dithiothreitol (DTT) for 1 h at 55° C. to reduce cysteines. After DTT was removed, 55 mM iodoacetamide (IAA) was added to alkylate cysteines for 45 min, followed by washing with a 50:50 mixture of 25 Mm ABC and ACN for 3 times. Lys-C/trypsin was added to cover each gel piece and incubated in barocycler at 50° C. (120 cycles of 20 kpsi for 50 seconds and atmospheric pressure for 10 sec) for digestion. Peptides from gel pieces were extracted by adding 60% ACN/5% trifluoroacetic acid (TFA) with sonication, and the dry peptide pellet was resuspended in 94.9% water, 3% ACN, 0.1% formic acid (FA). The samples were run on a nano Eksigent 425 HPLC system coupled to the Triple TOF 5600 plus (Sciex, Framingham, Mass.). The peptides were loaded onto a Sciex NanoLC Chrom XP C18 trap column (350 µm×0.5 mm) for concentration, and this enrichment column was switched to the nano flow path after 5 min. Peptides were separated using the reversed phase 3C18-CL C18 analytical column (75 µm×150 mm) from Sciex. The sample was injected into the Triple TOF 5600 plus through the Nanospray III source fitted with an emission tip from New Objective. Peptides from the digestion were eluted from the columns using a mobile phase A (0.1% formic acid in $H_2O$) and a mobile phase B (0.1% formic acid in ACN). With a flow rate of 300 nL/min, the method began at 95% A for 1 min followed by a gradient of 5% B to 35% B in 61 min and from 35% B to 80% B in 1 min. 80% B was held for 6 min, then brought to 5% B, and held for 20 min. Data acquisition was performed monitoring 50 precursors at an accumulation time of 250 ms/scan. Database searches of the UniProt_human proteins were performed using Mascot Daemon v.2.5.1 (Matrix Science) with peptide mass tolerance of 0.05 Da and fragment mass tolerance of 0.2 Da. The false discovery rate (FDR) was adjusted to 5%. Among the identified proteins, proteins with (i) no relevance (e.g. keratin), (ii) molecular weight with much discrepancy with one estimated from gel, (iii) Mascot protein score below the 5% confidence threshold, and (iv) exponentially modified protein abundance index (emPAI), an estimation of protein abundance, less than 1.0 were excluded. The selected proteins were matched to the identified proteins from albumin stock solution.
Figure 15:
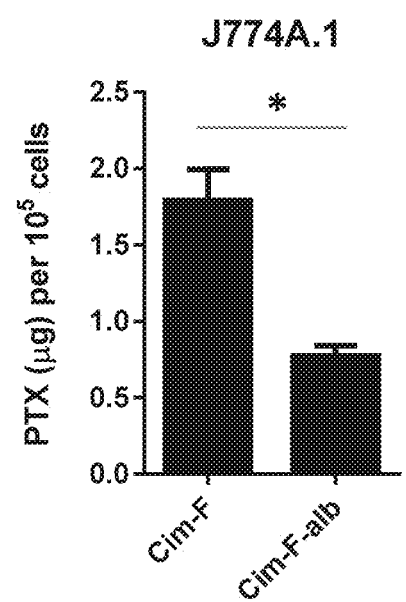
FIG. 15. PTX uptake by J774A.1 macrophages after 3 h incubation at 37° C. with Cim-F and Cim-F-alb (equivalent to 30 µg/mL PTX) in serum containing media. n=3 replicates. *: p<0.01 by two-tailed unpaired t-test.

The NC were produced with commercially available albumin, but SDS-PAGE analysis found additional proteins to be associated with the NC (FIG. 14). The non-albumin proteins, identified by LC-MS/MS, are attributable to impurities incompletely removed from human serum plasma during the production. Interestingly, Cim-C-alb showed more intense non-albumin bands than PNC-alb and Cim-F-alb. The preferential enrichment of non-albumin proteins is attributed to the cationic surface of Cim-C.

We then analyzed the conformation of albumin bound to NC. Typical methods to assess the protein conformation, such as circular dichroism and synchronous fluorescence spectroscopy, were not suitable for analyzing the surface-bound albumin because they require the protein solution contain no substances to interfere with optical measurements. Therefore, we resorted to pulse proteolysis for evaluating the status of albumin bound to NC [30]. The principle of pulse proteolysis is that folded and unfolded proteins have different susceptibilities to proteolysis: i.e., protease exposed to a mixture of unfolded and folded proteins for a short time will preferentially digest unfolded proteins. Accordingly, the extent of protein unfolding can be estimated based on the band intensity of intact protein in the gel electrophoresis. When NC were subjected to pulse proteolysis by thermolysin, Cim-C-alb showed the highest degree of digestion (67.8±13.4%) (FIG. 4a, b). PNC-alb and Cim-F-alb showed similar fractions of digestion of 18.4±7.2% and 14.5±2.6%, respectively. This indicates that albumin on Cim-C-alb was more unfolded than those of PNC-alb and Cim-F-alb.

Albumin has esterase-like activity [41], which is affected by its conformation change [42]. Therefore, the extent of intact (i.e., active) albumin can be determined by measuring its ability to hydrolyze pNPA to p-nitrophenol. PNC-alb and Cim-F-alb showed similar % active albumin, but Cim-C-alb showed much lower % active albumin (FIG. 4c). This indicates that albumin on Cim-C-alb underwent greater conformation change than PNC-alb and Cim-F-alb, consistent with the proteolysis assay.

Cellular Uptake of PNC-alb, Cim-C-alb, and Cim-F-alb by Macrophages and Cancer Cells We expected that NC-cell interactions would be affected by the surface-bound albumin. Cellular uptake of NC was tested with J774A.1 murine macrophages and B16F10 melanoma cells, which represent the MPS and cancer cells overexpressing SPARC [43], respectively. The extent of cellular uptake of NC was measured by analyzing the PTX content in the collected cell pellets after a shot term exposure of NC to the cells. The NC concentration was kept at 30 µg/mL, much higher than 9.6 µg/mL, the solubility of amorphous PTX in 10% FBS measured in 6 h, so that the majority of NC remain intact during the incubation period (30 min or 3 h).

In J774A.1 macrophages, Cim-C-alb was taken up significantly more than PNC-alb and Cim-F-alb (FIG. 5a). Thifference between PNC-alb and Cim-F-alb was insignificant. Cellular uptake of Cim-C-alb at 4° C. was significantly lower than that at 37° C. and not different from those of PNC-alb and Cim-F-alb, indicating that the relatively high Cim-C-alb uptake was energy-dependent endocytosis. The macrophage uptake of Cim-C-alb is attributable to the conformation change of the surface bound albumin, which may have been recognized by scavenger receptors of macrophages. To test this, macrophages were pretreated with polyinosinic acid, a known inhibitor of scavenger receptor-mediated endocytosis [44]. After polyinosinic acid treatment, macrophage uptake of Cim-C-alb was reduced to the same level as other NC (FIG. 5b). Neither PNC-alb nor Cim-F-alb uptake was affected by polyinosinic acid treatment. This result confirms that Cim-C-alb with denatured albumin was preferentially taken up by macrophages via scavenger receptors. In contrast, PNC-alb and Cim-F-alb with more native albumin avoided the scavenger receptor-mediated endocytosis by macrophages, resulting in relatively small macrophage uptake. The albumin on Cim-F-alb rather helps reduce macrophage uptake of the NC (Supporting FIG. 5), consistent with its dysopsonin function reported in the literature [25, 26].

Figure 6:
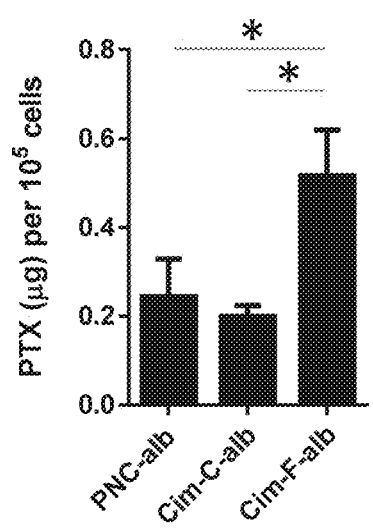
FIG. 6.
Figure 6:
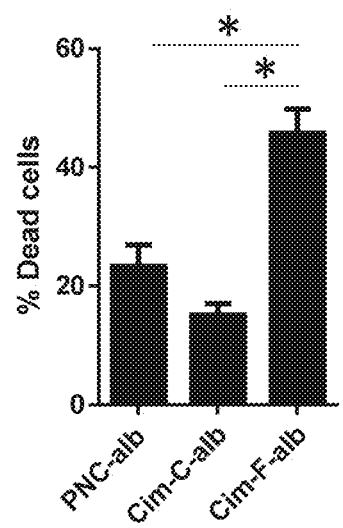
Figure 6:
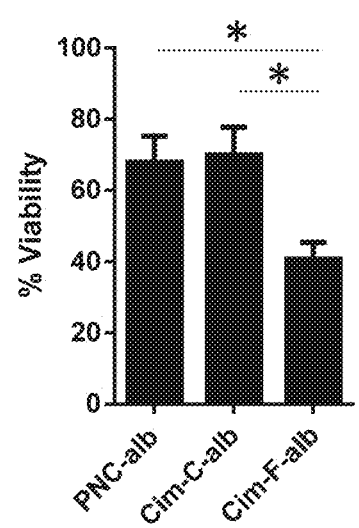
Figure 16:
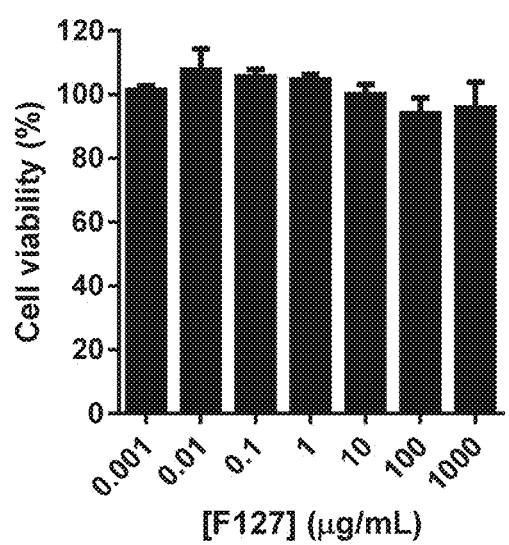
FIG. 16.
Figure 16:
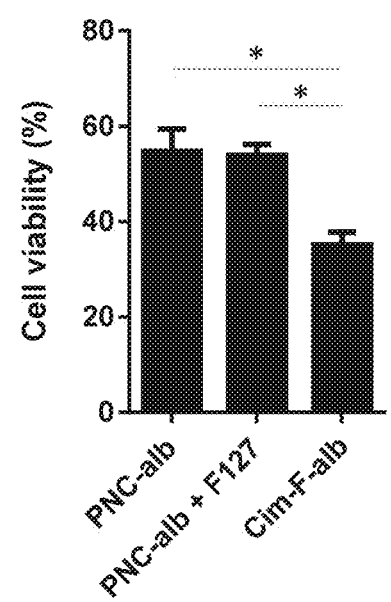

NC uptake by B16F10 cells showed a different trend. Cim-F-alb was taken up most by B16F10 cells, and Cim-C-alb least (FIG. 6a). Consistent with the cellular uptake, Cim-F-alb treatment induced greater cell death (FIG. 6b) and lower metabolic activity (FIG. 6c) in B16F10 cells than PNC-alb and Cim-C-alb. We confirmed that the relatively high cytotoxicity of Cim-F-alb was not due to F127, which constitutes 1.6 wt % of the total NC mass. F127 itself did not have any toxicity in B16F10 cells at a concentration up to 1 mg/mL (Supporting FIG. 6). PNC-alb mixed with 10 µg/mL F127 (18 times higher than the F127 content in Cim-F-alb at an equivalent PTX dose) showed the same level of cytotoxicity as PNC-alb and lower toxicity than Cim-F-alb (FIG. 16). This confirms that there was no additional cytotoxicity attributable to F127. In other words, the relatively high cytotoxicity of Cim-F-alb is a consequence of the enhanced cellular uptake, not the effect of residual F127. The preferential uptake of Cim-F-alb by B16F10 cells is attributed to the native conformation and arrangement of the surface-bound albumin, which facilitates its interaction with SPARC expressed on B16F10 cells. PNC-alb and Cim-F-alb had comparable albumin contents (FIG. 13, 14). Pulse proteolysis and esterase activity indicate that the conformations of albumin bound to the two NC were also similar (FIG. 4). However, the significant difference in zeta potential (FIG. 13) suggests that the orientation of albumin on the NC surface have been affected by the nature of the exposed surface. Between hydrophobic PNC surface and hydrophilic Cim-F surface, the latter may have provided a favorable platform for albumin to position itself to interact with SPARC. It is also possible that the small size of Cim-F-alb has contributed to the greater uptake by B16F10 cells than PNC-alb uptake. Cim-C-alb did not have advantages in either size or albumin conformation, which accounts for their relatively low cellular uptake and activity in B16F10 cells.

To confirm the involvement of albumin in Cim-F-alb uptake process, B16F10 cells were incubated with Cim-F (NC identically prepared omitting albumin coating) and Cim-F-alb. PTX uptake was greater with Cim-F-alb (FIG. 7a), confirming the contribution of albumin to cellular uptake of the NC. Cim-F-alb uptake by B16F10 cells was inhibited in the presence of ≥20 mg/mL of albumin (FIG. 7b). This result indicates that Cim-F-alb and albumin share the same receptor, consistent with the native conformation. It is also worth noting that the competition for the common receptor occurs at ≥20 mg/mL, higher than typical albumin concentration in tissue interstitium [45]. This suggests that cellular uptake of Cim-F-alb may not be much affected by interstitial albumin. However, we cannot exclude the possibility that some tumors have higher level of interstitial albumin than normal tissues and may negatively impact cellular uptake of Cim-F-alb.

Figure 17:
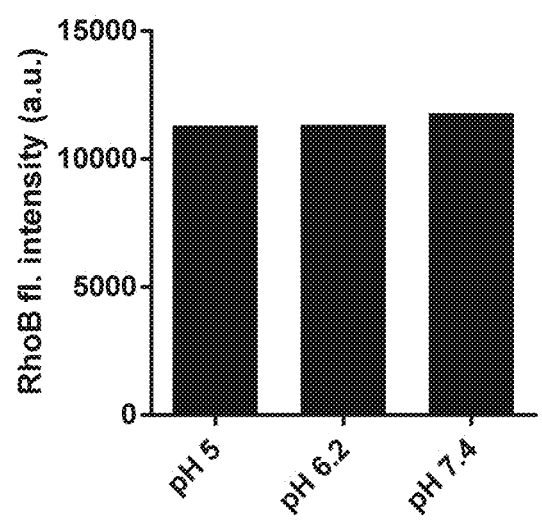
FIG. 17. Fluorescence intensity of Rhodamine B at different pH's.
Figure 18:
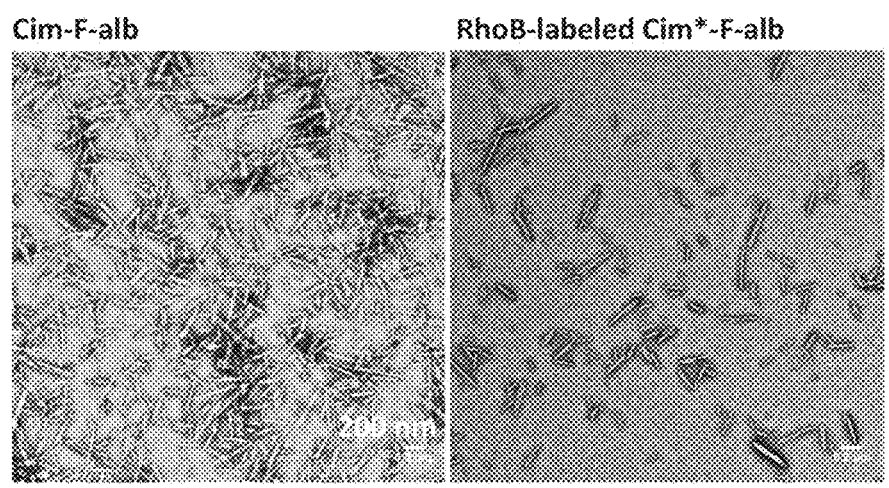
FIG. 18. TEM images of Cim-F-alb and RhoB-labeled Cim*-F-alb.
Figure 19:
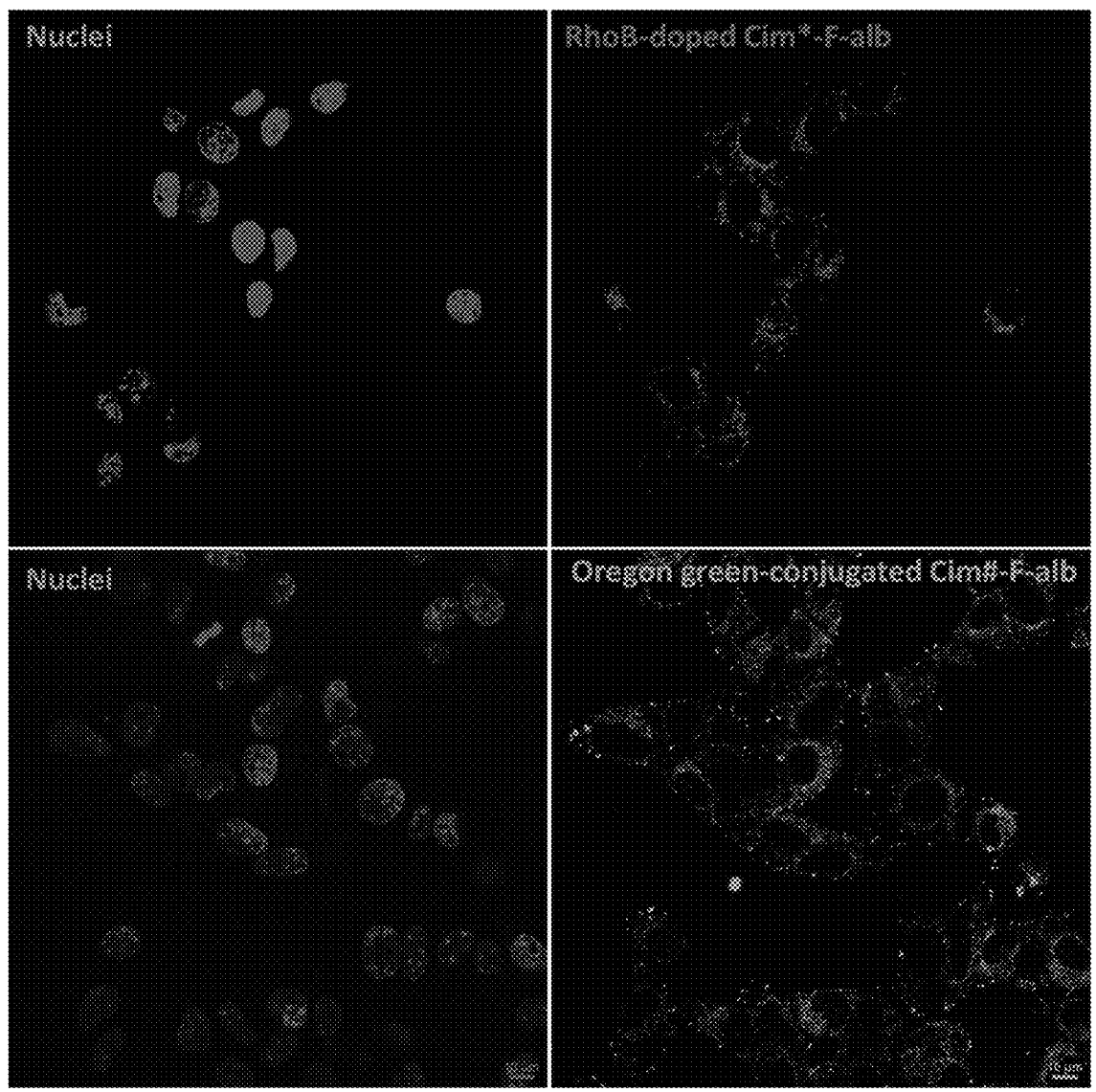
FIG. 19. Intracellular localization of rhodamine B doped Cim*-F-alb (Top) or Oregon green-conjugated Cim#-F-alb (bottom) in B16F10 cells after 30 min incubation.
Figure 20:
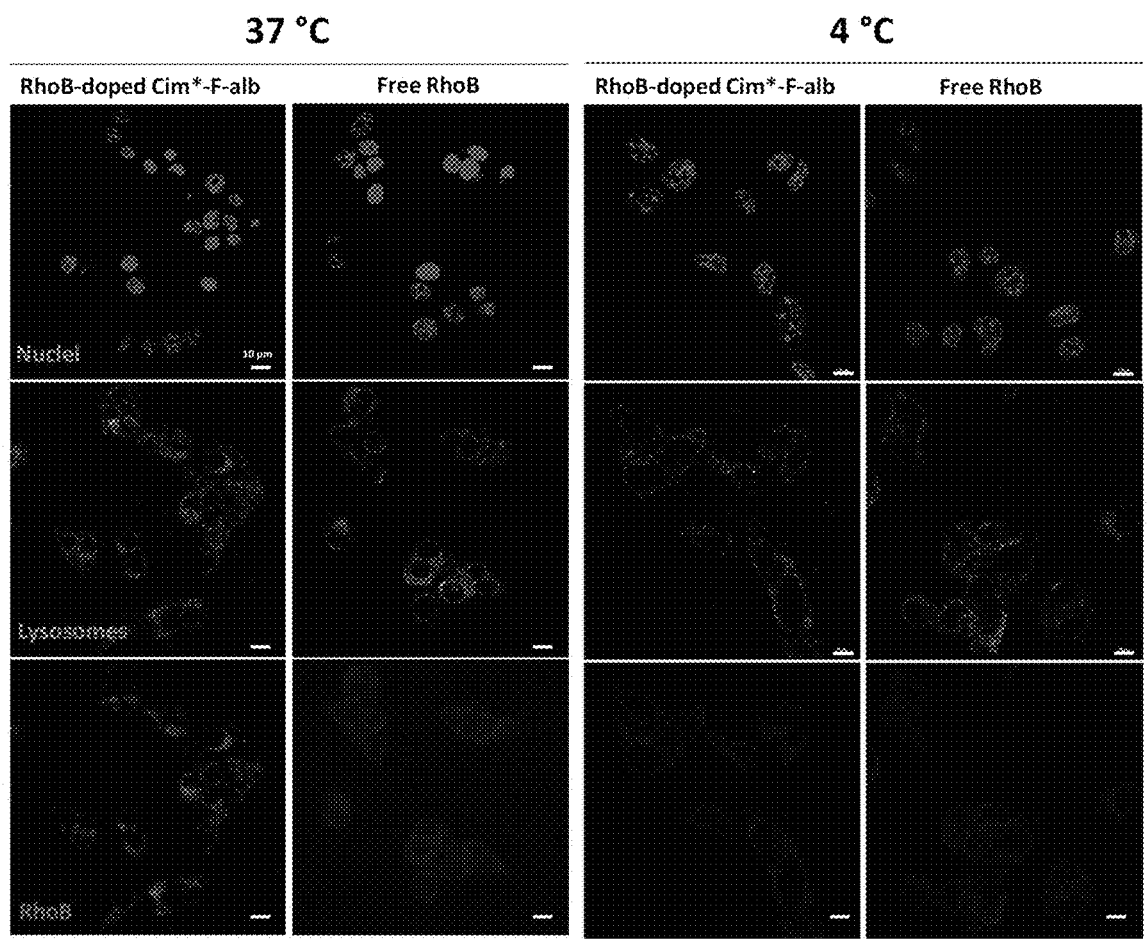
FIG. 20. Intracellular localization of RhoB doped Cim*-F-alb in B16F10 cells after 30 min incubation at 37° C. or 4° C. Scale bar: 10 µm.
Figure 21:
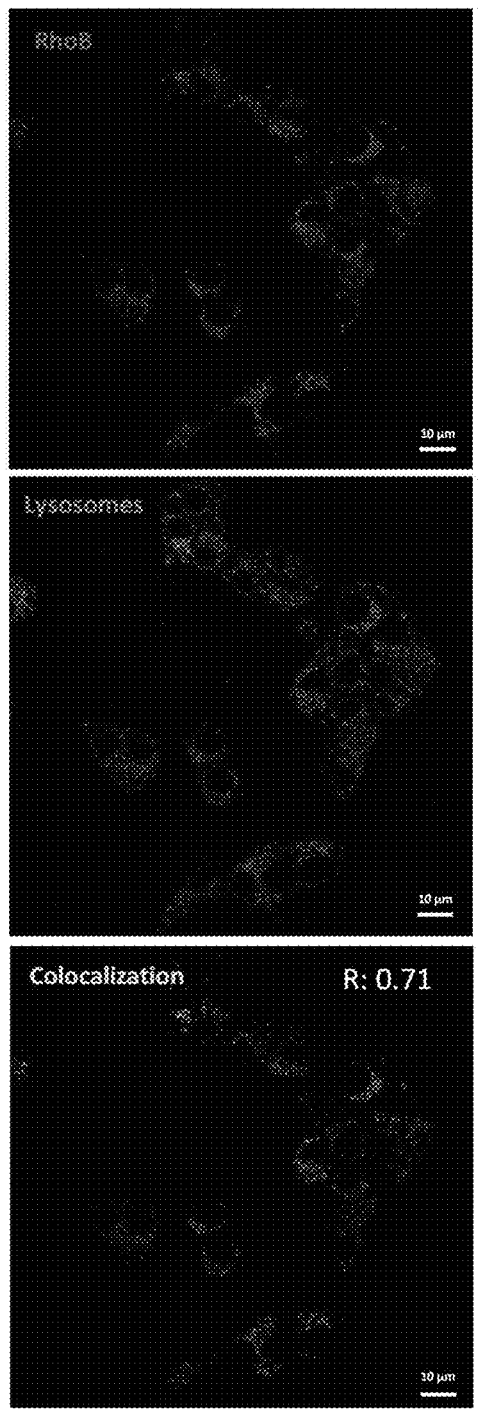
FIG. 21. Assessment of colocalization of Cim*-F-alb with Lysotracker. The degree of colocalization was analyzed by using Coloc 2 plugin of ImageJ. Pearson's correlation coefficient (R) represents the degree of colocalization: R=1 (perfect colocalization), R=0 (no colocalization), R=−1 (perfect exclusion).

Cim-F-alb taken up by B16F10 cells was located with confocal microscopy. Cim-F-alb was fluorescently labeled by doping with a small quantity of rhodamine B. We chose rhodamine B as a fluorescence marker for tracing Cim-F-alb uptake, because the dye maintained constant fluorescence intensity at a pH range of 5 to 7 (FIG. 17), suitable for intracellular imaging. It is well established that an organic dye such as rhodamine B can be stably incorporated in organic crystal lattice with minimal change in crystallization behavior [29], and NC similarly doped with fluorescent dyes have previously been used to visualize their cellular uptake [46]. To ensure that the incorporated rhodamine B represents Cim-F-alb, free rhodamine B was tested in parallel. In addition, another set of labeled Cim-F-alb was prepared by replacing a small fraction of PTX with Oregon green-conjugated PTX (Cim#-F-alb) and compared with Cim*-F-alb. The rhodamine B-doped NC (Cim*-F-alb) showed the same size and shape as Cim-F-alb and thus qualified as its representative (Supporting FIG. 8). B16F10 cells incubated with Cim*-F-alb for 30 min showed punctate signals of rhodamine B (FIG. 7c). Those incubated with an equivalent dose of free rhodamine B only showed dim diffuse fluorescence, indicating that the punctate signals shown with Cim*-F-alb represent NC, not the dye leached out of the NC. B16F10 cells treated with Cim#-F-alb (covalently labeled Cim-F-alb) also showed punctate signals similar to those of Cim*-F-alb, confirming the cellular uptake of Cim-F-alb (FIG. 19). The NC uptake was completely abolished at 4° C. (FIG. 20). The fluorescence of Cim*-F-alb overlapped with that of LysoTracker (FIG. 7d) with a Pearson's correlation coefficient (R) of 0.71 (FIG. 21), which indicates a high degree of colocalization (perfect colocalization: R=1; no colocalization: R=0; and perfect exclusion: R=−1). These results show that Cim*-F-alb were taken up by the energy-dependent endocytosis pathway and partly trafficked to late-endo/lysosomes.

The in vitro cellular uptake studies identify Cim-F-alb as the most desirable NC among the three types of NC. Cim-F-alb shows less macrophage uptake than Cim-C-alb and greater uptake by B16F10 melanoma cells than PNC-alb and Cim-C-alb, most likely due to the small size and favorable albumin conformation and arrangement on the surface. Therefore, Cim-F-alb was used in the subsequent studies.

Dissolution of Cim-F-alb

Figure 22:
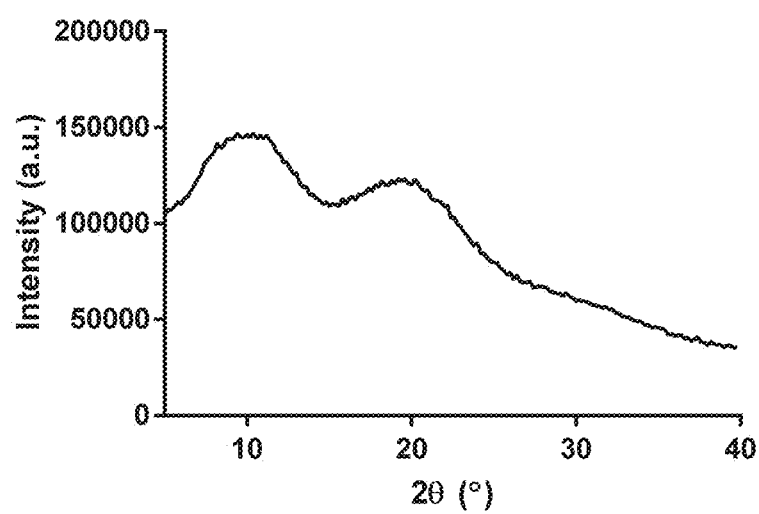
FIG. 22. X-ray diffraction patterns of as-received PTX.

To predict the circulation stability of Cim-F-alb, we evaluated the dissolution of Cim-F-alb in PBS and undiluted FBS, comparing with Abraxane, a commercial albumin-bound PTX formulation. The as-received PTX, which was amorphous (FIG. 22), dissolved in 10% FBS, 50% FBS, and undiluted FBS up to 9.6±2.6 µg/mL, 47.5±11.4 µg/mL, 71.9±8.2 µg/mL, respectively, in 6 h at 37° C. (FIG. 23). Due to the crystallinity, we expected that Cim-F-alb would dissolve in each medium no more than the measured values at comparable conditions.

Particle dissolution was monitored by light scattering according to the method reported by Anhalt et al. [47], which depends on the linear relationship between the number of particles and absolute scattering intensities (i.e., derived count rate). The scattering intensity of particle suspension decreases in proportion to the solid content in the suspension. When the particles completely dissolve, the scattering intensity matches that of blank medium. Therefore, if the particles dissolve in a medium, the scattering intensity vs.

concentration plot shows two linear segments with distinct slopes: a flat segment followed by the second segment with a slope corresponding to the increasing solid fraction [47]. The solubility is calculated from the intersection point of the two segments.

Abraxane in PBS and FBS followed this pattern, with solubility of 25 µg/mL and 75 µg/mL (as PTX equivalent), respectively (FIG. 8a). Twenty five µg/mL is higher than the solubility of amorphous as-received PTX in PBS we reported previously (~0.2 µg/mL [9]). This may be explained by the solubilizing effect of albumin present in the Abraxane formulation (225 µg/mL albumin in Abraxane eq. to 25 µg/mL PTX) in addition to its amorphous status (FIG. 24). The solubility of Abraxane in FBS (75 µg/mL) was comparable to amorphous PTX solubility in FBS (71.9. µg/mL). The linearity of scattering intensity vs. concentration plot started to disappear as soon as in 1 h, indicating that the dissolution occurred quickly, which is consistent with the literature [48]. The PTX dissolved in FBS over 6 h was proportional to the concentration of Abraxane, which further confirms complete dissolution of Abraxane up to 75 µg/mL (FIG. 23). In contrast, Cim-F-alb in PBS showed a linear relationship over the entire concentration range without evident change in slope, which indicates that Cim-F-alb remained as particles at all concentrations tested. The linear pattern was persistent in FBS, with slight decrease in the slope attributable to partial dissolution of PTX (no higher than 8.3±3.0 µg/mL when measured after 6 h incubation, FIG. 23). The contrast between Abraxane and Cim-F-alb in FBS is worthwhile to note. This suggests that Abraxane in blood will dissociate into albumin-bound PTX molecules at <75 µg/mL, whereas Cim-F-alb in blood will mostly remain as nanoparticles at least for 24 h.

The dissolution of Abraxane and Cim-F-alb in FBS was monitored over time to confirm this difference in the stability in serum. Abraxane in FBS was immediately indistinguishable from FBS at 2 µg/mL and 30 µg/mL, indicating its rapid dissolution (FIG. 8b). On the other hand, Cim-F-alb in FBS showed higher count rates than that of FBS over 15 min (duration of observation), indicating that Cim-F-alb maintained the particle status at both concentrations. We may predict the fates of systemically administered Abraxane and Cim-F-alb based on these results. Considering that the typical PTX dose in mice is 15-40 mg/kg in a blood volume of 1.5-2.5 mL [49], the initial PTX concentration is expected to be 120-533 µg/mL. At this concentration range, Cim-F-alb is likely to circulate as nanoparticles, whereas Abraxane will dissociate instantaneously into individual albumin molecules bound to PTX. In other words, during the initial circulation and biodistribution phase, Cim-F-alb and Abraxane will circulate in different forms—nanoparticles and PTX-bound albumin molecules, respectively.

We then compared Cim-F-alb, Abraxane, and solvent-dissolved PTX with respect to the cytotoxicity. All three groups showed similar dose response curves with comparable $IC_{50}$ values irrespective of the cell lines, treatment conditions, or assay methods (Table 1, FIG. 25). One-way ANOVA analysis of $IC_{50}$ values indicated no statistically significant difference between groups. This result indicates that Cim-F-alb, dissolved in the medium and/or taken up as NC (at the higher end of the concentration range: 50,000 and 100,000 nM, in particular), provided similar effects as free drug or Abraxane.

TABLE 1

$IC_{50}$ values of free PTX, Abraxane, and Cim-F-alb

| Cell lines | Treatment conditions | Assay methods | Free PTX (nM) | Abraxane (nM) | Cim-F-alb (nM) | Comparison* |
|---|---|---|---|---|---|---|
| SKOV3 | 24 h treatment + 48 h post-treatment incubation | MTT assay | 34.21 | 38.11 | 37.20 | No statistical difference (p = 0.8508) |
| B16F10 | 24 h treatment | PI staining + flow cytometry | 423.1 | 548.3 | 454.3 | No statistical difference (p = 0.8842) |
| B16F10 | 24 h treatment + 12 h post-treatment incubation | MTT assay | 91.30 | 76.58 | 94.34 | No statistical difference (p = 0.7708) |
| B16F10 | 24 h treatment + 24 h post-treatment incubation | MTT assay | 213.3 | 280.0 | 245.2 | No statistical difference (p = 0.7235) |
| B16F10 | 24 h treatment + 48 h post-treatment incubation | MTT assay | 765.1 | 806.0 | 926.7 | No statistical difference (p = 0.7548) |

*Extra sum-of-squares F test (Prism 6.0)

In Vivo Evaluation of Cim-F-Alb

We tested if PTX circulating as nanoparticles would have any advantages over Abraxane in antitumor effects. According to the prevalent premise of nanomedicine, nanoparticles can provide greater tumor accumulation than free drug by reducing renal clearance and allowing for selective access to tumors [50, 51]. Cim-F-alb is uniquely suited for testing this hypothesis because it contains the same components as Abraxane (albumin and PTX) but differs from Abraxane in the circulation stability. This allows us to exclude the potential contribution of the carrier materials, which often account for the majority of nanoparticle mass and add confounding effects to the therapeutic outcomes [52].

Figure 9:
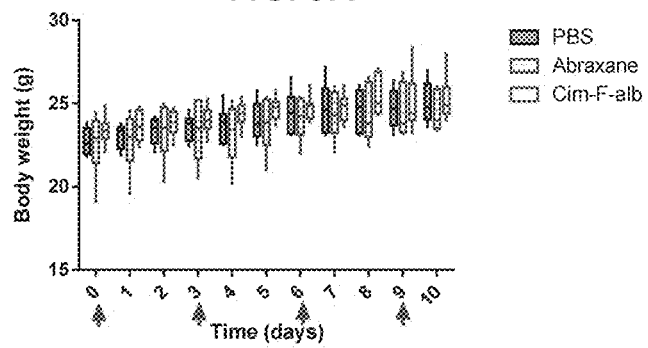
FIG. 9A Body weight change of animals receiving PBS, Abraxane or Cim-F-alb, expressed in box-and-whisker plot. The box extends from the 25th to 75th percentiles, the line in the middle of the box indicates the median, and the whiskers go down to the smallest value and up to the largest.
FIG. 9B Box-and-whisker plot of B16F10 tumor volumes: Mice were treated with PBS (black; n=6), Abraxane (blue; n=6), or Cim-F-alb (red; n=7) at 15 mg/kg q3d×4. Arrows indicate treatment times. One mouse in each of the Abraxane and PBS group was sacrificed on day 7 due to the large size of the tumor.
FIG. 9C Specific growth rate of B16F10 tumor=Δ log V/Δt (V: tumor volumes; t: time in days). Horizontal bars=means. *: p<0.05 by Tukey's multiple comparisons test.
Figure 9:
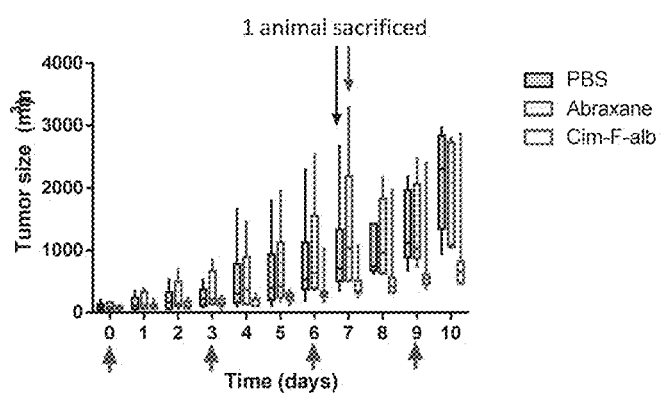
Figure 9:
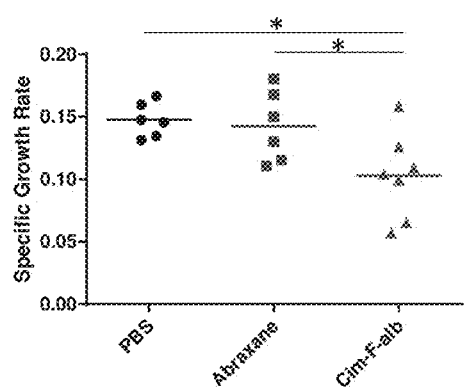

Cim-F-alb or Abraxane equivalent to 15 mg/kg PTX was administered to C57BL/6 mice bearing subcutaneous B16F10 tumors by tail vein injection on days 0, 3, 6, and 9 (total PTX dose=60 mg/kg). Cim-F-alb was well tolerated at this dose and caused no significant loss of body weight (FIG. 9a) or abnormal blood chemistry (data not shown). This dose was also below the reported maximum tolerated dose of Abraxane [8]. Therefore, 15 mg/kg q3d×4 was considered a sufficiently safe condition to test the anti-tumor activities of two formulations. At this dose, Abraxane did not attenuate the growth of B16F10 tumors as compared to PBS control (FIG. 9b). On the other hand, Cim-F-alb treatment resulted in significant delay in tumor growth (p<0.01 vs PBS or Abraxane, Tukey's multiple comparisons test). One mouse in each of the PBS and Abraxane-treated groups had to be sacrificed on day 7 according to the humane endpoint, and all animals in these groups had tumors with ≥1000 mm$^3$ in size by day 10. In contrast, there was only one animal with a tumor >1000 mm$^3$ in the Cim-F-alb treated group on day 10. Tumor growth was also expressed as the specific growth rate, which is appropriate in assessing the exponential growth of tumor [33] (FIG. 9c). The Cim-F-alb group showed a significantly lower specific growth rate than the PBS- or Abraxane-treated groups (p<0.05 vs. both groups, Tukey's multiple comparisons test). To compare the effect of treatment on the tissue level, tumors collected one day after the last dose were analyzed with respect to the number of apoptotic cells and the PTX content. Tumor sections from the Cim-F-alb group showed a significantly higher number of TUNEL+apoptotic cells than those of PBS- or Abraxane-treated groups (FIG. 10a, b, FIG. 26, 27). Consistently, the PTX content in tumor was significantly higher in the Cim-F-alb group (27.4±22 μg/g) than in the Abraxane treatment group (13.8±6 μg/g) (FIG. 10c).

We examined if the superior performance of Cim-F-alb relative to Abraxane was due to preferable cellular uptake of the NC. Macrophages exposed to Cim-F-alb and Abraxane for 30 min showed no difference in PTX uptake (FIG. 28), which may be explained by the fact that both are small enough to avoid phagocytic uptake. Cim-F-alb uptake by B16F10 cells in 3 h were rather less than Abraxane uptake (FIG. 28). This suggests that, with both Cim-F-alb and Abraxane containing albumin that helps interact with SPARC-positive B16F10 cells, the molecularly dispersed Abraxane be more efficient than nanopaticulate Cim-F-alb in entering the cancer cells. Therefore, the advantage of Cim-F-alb over Abraxane is not at the cellular level.

Determination of Maximum Tolerated Dose (MTD) of Cim-F-alb

All mice receiving PTX 90 mg/kg and PTX 60 mg/kg groups had to be sacrificed during the treatment period due to the excessive body weight loss (FIG. 29). In contrast, no significant change in body weight was observed in animals receiving PTX 30 mg/kg and 15 mg/kg. Therefore, MTD was determined to be PTX 30 mg/kg every 3 days×5 times. No significant abnormality was observed in blood serum in mice in PTX 30 mg/kg q3d×5 group (data now shown).

In Vivo Antitumor Activity Evaluation

At PTX 30 mg/kg every 3 days×5 times, Abraxane and Cim-F-alb extended the median survival by 4 days and 10 days, respectively, compared to PBS control (FIG. 30). No significant change in body weight due to the treatment was observed.

PK/BD Evaluation of Cim-F-alb

Figure 31A:
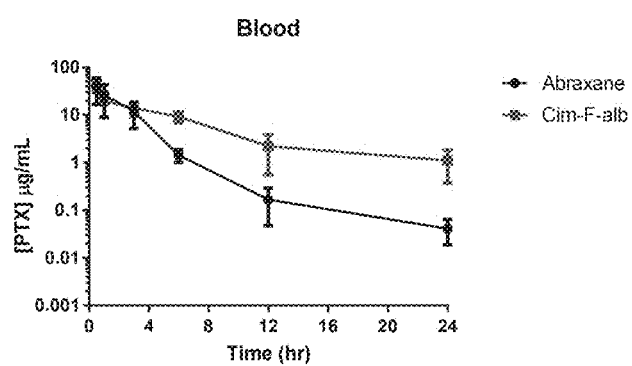
Figure 31B:
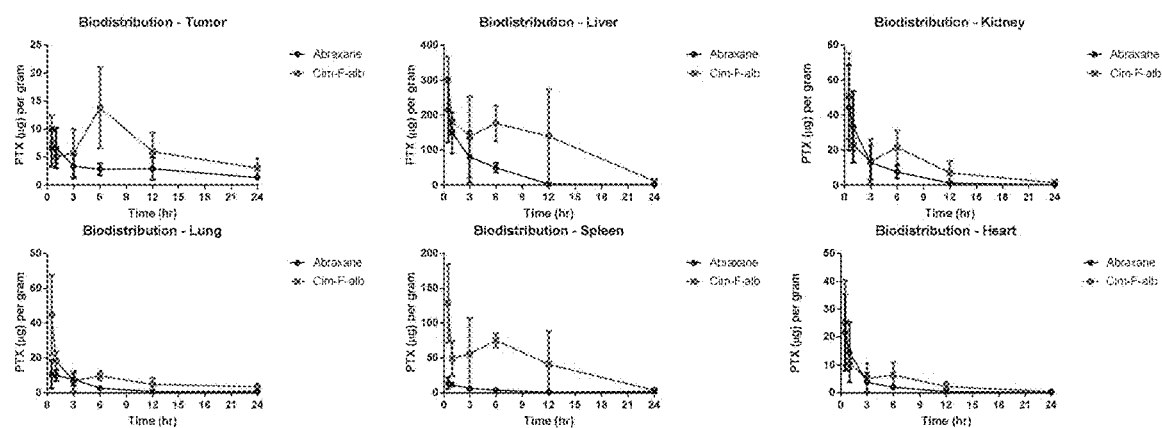

A higher drug level of Cim-F-alb was observed compared to Abraxane in blood, likely due to its crystalline status and lower solubility (FIG. 31a). Cim-F-alb also showed higher level in the liver and spleen than Abraxane due to its large size. In addition, a greater amount of drug was found in tumor of animals treated with Cim-F-alb as compared to those with Abraxane (FIG. 31b).

Application of Cim-F-alb Technique to Carfilzomib (CFZ)

CFZ/Cim-F-alb showed a rod shape under TEM (FIG. 32). The size measured by DLS was 258.3±17.6 nm (n=3) with a negative zeta potential of −12.8±2.0 mV. The drug content was 74±10 wt %, with albumin consisting 24 wt %. CFZ/Cim-F-alb maintained a linear relationship between the derived count rate and the concentration (FIG. 33), which indicates that CFZ/Cim-F-alb did not dissolve in PBS and FBS but rather exists as NC in the tested concentration range.

Application of Cim-F-alb technique to docetaxel (DTX)

DTX/Cim-F-alb showed a rod shape under TEM (FIG. 34). The size measured by DLS was 247.1±6.8 nm (n=3) with a polydispersity index value of 0.153±0.03. The drug content was 68.4±9.0 wt %, with albumin accounting for 18 wt %. DTX/Cim-F-alb maintained a linear relationship between the derived count rate and the concentration in 10 and 50% FBS (FIG. 35), which indicates that DTX/Cim-F-alb did not dissolve in serum-containing media but rather exists as NC in the tested concentration range Taken together, these results support that Cim-F-alb circulating as nanoparticles have reached tumors better than Abraxane which dissociates into PTX-bound albumin molecules upon intravenous injection. The in vitro cell studies and dissolution tests let us predict that the surface-bound albumin and particle stability in serum may contribute to the preferential tumor accumulation and retention of Cim-F-alb. The pharmacokinetics and biodistribution of the two formulations support our predictions.

Example: Nanocrystals to Avoid Uptake in the Reticuloendothelial System (RES)

In another example, slowly dissolving nanocrystals may be modified with a protective surface agent to avoid recognition by the RES system and prolong their circulation time.

Example: Anti-Cancer Drugs

Nanocrystals (NCs) of water-insoluble drugs with a size between 100 and 300 nm can take advantage of the enhanced permeability and retention (EPR) effects to reach tumors. As disclosed further herein, in at least one embodiment, surface modification with albumin may leverage the potential benefit of NCs by prolonging the circulation time and improving interaction with target cells as compared to non-modified NCs or PEG-modified NCs. The rationale is that native albumin avoid immune recognition as self-protein and can interact with tumor microenvironment via secreted protein acidic and rich in cysteine (SPARC) protein. One can therefore produce albumin-coated paclitaxel NCs with a size appropriate for intravenous application. Human serum albumin (HSA) functionalized PTX NCs were made by the anti-solvent method ("PNC-alb") or a new method involving a surfactant ("Cim-C-alb" and "Cim-F-alb"). Size, crystallinity, and albumin content of NCs were compared. Albumin-mediated cellular uptake was also studied. Solubility, dissolution rate, and cytotoxicity study indicate that Cim-F-alb circulate in the blood as NCs and eventually dissolve to exert cytotoxicity upon dilution. Cim-F-alb showed less macrophage uptake and greater cytotoxic effect on SPARC+ cancer cells than other NCs, likely due to the abundance of native albumin on the surface.

Those skilled in the art will recognize that numerous modifications can be made to the specific implementations described above. The implementations should not be limited to the particular limitations described. Other implementations may be possible. In addition, all references cited herein are indicative of the level of skill in the art and are hereby incorporated by reference in their entirety.

REFERENCES

1. Merisko-Liversidge, E. M. and G. G. Liversidge, *Drug Nanoparticles: Formulating Poorly Water-Soluble Compounds*. Toxicol Pathol, 2008. 36(1): p. 43-48.
2. Yuan, F., et al., *Vascular permeability in a human tumor xenograft: molecular size dependence and cutoff size*. Cancer Res, 1995. 55(17): p. 3752-6.
3. Liu, F., et al., *Targeted cancer therapy with novel high drug-loading nanocrystals*. J Pharm Sci, 2010. 99(8): p. 3542-51.
4. Lu, Y., et al., *Development and evaluation of transferrin-stabilized paclitaxel nanocrystal formulation*. J Control Release, 2014. 176: p. 76-85.
5. Fuhrmann, K., M. A. Gauthier, and J. C. Leroux, *Targeting of injectable drug nanocrystals*. Mol Pharm, 2014. 11(6): p. 1762-71.
6. Mouton, J. W., et al., *Pharmacokinetics of itraconazole and hydroxyitraconazole in healthy subjects after single and multiple doses of a novel formulation*. Antimicrob Agents Chemother, 2006. 50(12): p. 4096-102.
7. Gao, L., et al., *Studies on pharmacokinetics and tissue distribution of oridonin nanosuspensions*. Int J Pharm, 2008. 355(1-2): p. 321-7.
8. Shegokar, R. and K. K. Singh, *Surface modified nevirapine nanosuspensions for viral reservoir targeting: In vitro and in vivo evaluation*. Int J Pharm, 2011. 421(2): p. 341-52.
9. Murakami, M., et al., *Docetaxel Conjugate Nanoparticles That Target alpha-Smooth Muscle Actin-Expressing Stromal Cells Suppress Breast Cancer Metastasis*. Cancer Res, 2013. 73(15): p. 4862-71.
10. Müller, R. H., S. Gohla, and C. M. Keck, *State of the art of nanocrystals—Special features, production, nanotoxicology aspects and intracellular delivery*. European Journal of Pharmaceutics and Biopharmaceutics, 2011. 78(1): p. 1-9.
11. Merisko-Liversidge, E. and G. G. Liversidge, *Nanosizing for oral and parenteral drug delivery: A perspective on formulating poorly-water soluble compounds using wet media milling technology*. Adv Drug Deliv Rev, 2011. 63(6): p. 427-440.
12. Keck, C. M. and R. H. Müller, *Drug nanocrystals of poorly soluble drugs produced by high pressure homogenisation*. European Journal of Pharmaceutics and Biopharmaceutics, 2006. 62(1): p. 3-16.
13. Merisko-Liversidge, E., G. G. Liversidge, and E. R. Cooper, *Nanosizing: a formulation approach for poorly-water-soluble compounds*. European Journal of Pharmaceutical Sciences, 2003. 18(2): p. 113-120.
14. Sun, B. and Y. Yeo, *Nanocrystals for the parenteral delivery of poorly water-soluble drugs*. Current Opinion in Solid State and Materials Science, (0).
15. Juhnke, M., D. Martin, and E. John, *Generation of wear during the production of drug nanosuspensions by wet media milling*. European Journal of Pharmaceutics and Biopharmaceutics, 2012. 81(1): p. 214-222.
16. Begat, P., et al., *The effect of mechanical processing on surface stability of pharmaceutical powders: Visualization by atomic force microscopy*. J Pharm Sci, 2003. 92(3): p. 611-620.
17. Zhang, H., et al., *Preparation and antitumor study of camptothecin nanocrystals*. Int J Pharm, 2011. 415(1-2): p. 293-300.
18. Zhao, R., et al., *Hybrid Nanocrystals: Achieving Concurrent Therapeutic and Bioimaging Functionalities toward Solid Tumors*. Mol Pharm, 2011. 8(5): p. 1985-1991.
19. Lu, Y., et al., *Development and evaluation of transferrin-stabilized paclitaxel nanocrystal formulation*. J Control Release, 2013.
20. Liu, F., et al., *Targeted cancer therapy with novel high drug-loading nanocrystals*. J Pharm Sci, 2010. 99(8): p. 3542-3551.
21. Zhao, R., et al., *Hybrid Nanocrystals: Achieving Concurrent Therapeutic and Bioimaging Functionalities toward Solid Tumors*. Molecular Pharmaceutics, 2011. 8(5): p. 1985-1991.
22. Rowe, R. C., et al., *Handbook of Pharmaceutical Excipients*. 2006: Pharmaceutical Press.
23. Palmer, W. K., E. E. Emeson, and T. P. Johnston, *Poloxamer 407-induced atherogenesis in the C57BL/6 mouse*. Atherosclerosis, 1998. 136(1): p. 115-123.
24. Li, C., W. K. Palmer, and T. P. Johnston, *Disposition of poloxamer 407 in rats following a single intraperitoneal injection assessed using a simplified colorimetric assay*. J Pharm Biomed Anal, 1996. 14(5): p. 659-665.
25. Alkilany, A. M., et al., *Cellular uptake and cytotoxicity of gold nanorods: molecular origin of cytotoxicity and surface effects*. Small, 2009. 5(6): p. 701-8.
26. Niidome, T., et al., *PEG-modified gold nanorods with a stealth character for in vivo applications*. J Control Release, 2006. 114(3): p. 343-7.
27. Connor, E. E., et al., *Gold nanoparticles are taken up by human cells but do not cause acute cytotoxicity*. Small, 2005. 1(3): p. 325-7.
28. Anhalt, K., et al., *Development of a new method to assess nanocrystal dissolution based on light scattering*. Pharm Res, 2012. 29(10): p. 2887-901.
29. Abouelmagd, S. A., et al., *Release kinetics study of poorly water-soluble drugs from nanoparticles: Are we doing it right?* Molecular Pharmaceutics, 2015. 12(3): p. 997-1003.

The invention claimed is:

1. A nanoparticle composition comprising:
a drug crystalline, wherein the drug crystalline comprising a drug and a surfactant, wherein the surfactant is a nonionic triblock copolymer composed of a central hydrophobic chain of polyoxypropylene (PPG) flanked by two hydrophilic chains of polyoxyethylene (PEG), wherein the crystalline is formed by mixing the drug in a surfactant-containing solvent medium, and by evaporating the solvent to form a crystalline surface with the surfactant intimately associated with the drug;
and a native protein, wherein the native protein is coated to the drug crystalline, and wherein the protein to the drug crystalline ratio ranges from about 1:10 to about 5:10 and the nanoparticle ranges in size between about 100 nm to about 250 nm.

2. The nanoparticle composition according to claim 1, wherein the drug crystalline is paclitaxel (PTX), docetaxel (DTX), or carfdzomib (CFZ).

3. The nanoparticle composition according to claim 1, wherein the native protein is albumin (Alb).

4. The nanoparticle according to claim 1, wherein the native protein is selected from the group consisting of albumin, transferrin, antibodies and the combination thereof.

5. The nanoparticle composition according to claim 1 wherein the surfactant having the structure of a PEG/PPG/PEG copolymer.

6. The nanoparticle composition according to claim 1 wherein the drug is water-insoluble.

7. The nanoparticle composition according to claim 1 wherein the drug has prolonged circulation time with improved interaction with target cells.

8. A method for making nanoparticles according to claim 1, comprising:
  crystallizing a drug in a surfactant-containing solvent medium to form a crystalline incipient film wherein the surfactant is a nonionic triblock copolymer composed of a central hydrophobic chain of polyoxypropylene (PPG) flanked by two hydrophilic chains of polyoxyethylene (PEG);
  hydrating the crystalline incipient film with bath sonication to form hydrated suspension; and
  stabilizing the hydrated suspension with a surface modifier, wherein said surface modifier is adsorbed on the crystalline surface via the surfactant.

9. The method of claim 8, wherein the surface modifier is albumin.

10. The method of claim 8, wherein the surface modifier to the crystalline ratio ranges from about 1:10 to about 5:10.

11. The method of claim 8, wherein the surfactant having the structure of a PEG/PPG/PEG copolymer.

12. A method of determining a water-insoluble drug's antitumor activity in maximum tolerated dose in a patient, comprising: providing a nanoparticle of claim 1 to the patient, observing the body weight loss of the patient up to about 20%, determining the tumor size shrinkage at the maximum tolerated dose, wherein the water insoluble drug is PTX, the surfactant is having the structure of a PEG/PPG/PEG copolymer and the native protein is albumin.

* * * * *